(12) United States Patent
Xia et al.

(10) Patent No.: US 9,978,958 B2
(45) Date of Patent: May 22, 2018

(54) PHOSPHORESCENT EMITTERS WITH PHENYLIMIDAZOLE LIGANDS

(71) Applicants: Chuanjun Xia, Lawrenceville, NJ (US); Chun Lin, Yardley, PA (US); Gregg Kottas, Ewing, NJ (US); Zeinab Elshenawy, Holland, PA (US)

(72) Inventors: Chuanjun Xia, Lawrenceville, NJ (US); Chun Lin, Yardley, PA (US); Gregg Kottas, Ewing, NJ (US); Zeinab Elshenawy, Holland, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 464 days.

(21) Appl. No.: 13/798,668

(22) Filed: Mar. 13, 2013

(65) Prior Publication Data

US 2014/0054563 A1   Feb. 27, 2014

Related U.S. Application Data

(60) Provisional application No. 61/692,987, filed on Aug. 24, 2012.

(51) Int. Cl.
*H01L 51/50* (2006.01)
*H01L 51/00* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
CPC ............. H01L 51/0084; H01L 51/0085; H01L 51/0086; H01L 51/0087; H01L 51/0088;
(Continued)

(56) References Cited

U.S. PATENT DOCUMENTS 4,769,292 A   9/1988   Tang et al.
5,061,569 A   10/1991  VanSlyke et al.
(Continued)

FOREIGN PATENT DOCUMENTS

EP   0650955   5/1995
EP   1725079   11/2006
(Continued)

OTHER PUBLICATIONS

Wong et. al., "Multifunctional Iridium Complexes Based on Carbazole Modules as Highly Efficient Electrophosphors", 2006, Angew. Chem. Int. Ed., vol. 45, pp. 7800-7803.*
(Continued)

*Primary Examiner* — Andrew K Bohaty
*Assistant Examiner* — Dylan C Kershner
(74) *Attorney, Agent, or Firm* — Duane Morris LLP

(57) ABSTRACT

Phosphorescent materials are provided, where the materials comprise a coordination compound having at least one ligand $L_3$ having Formula (I):

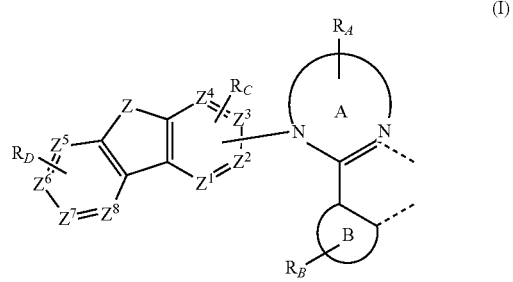

wherein A and B are each independently a 5-membered or 6-membered carbocyclic or heterocyclic ring; wherein $R_A$,
(Continued)

$R_B$, $R_C$, and $R_D$ each represent mono, di, tri, tetra substitutions, or no substitution; wherein $Z^1$, $Z^2$, $Z^3$, $Z^4$, $Z^5$, $Z^6$, $Z^7$, and $Z^8$ are each selected from N or C; wherein at least one of $Z^1$, $Z^2$, $Z^3$, $Z^4$, $Z^5$, $Z^6$, $Z^7$, and $Z^8$ is N; wherein one of $Z^1$, $Z^2$, $Z^3$, and $Z^4$ is C that is bonded to N of A; wherein Z is selected from the group consisting of BR, NR, PR, O, S, Se, C=O, S=O, SO$_2$, CRR', SiRR', and GeRR'; wherein R, R', $R_A$, $R_B$, $R_C$, and $R_D$ are described herein; wherein $L_3$ is coordinated to a metal $M_1$; and wherein $L_3$ may be linked with other ligands to comprise a tridentate, tetradentate, pentadentate, or hexadentate ligand. Devices, such as organic light emitting devices, comprising such compounds are also provided.

22 Claims, 3 Drawing Sheets

(51) Int. Cl.
    *C09K 11/06* (2006.01)
    *H05B 33/14* (2006.01)
    *C07F 15/00* (2006.01)

(52) U.S. Cl.
    CPC ...... *H05B 33/14* (2013.01); *C09K 2211/1007* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/5016* (2013.01)

(58) Field of Classification Search
    CPC .. H01L 51/50; H01L 51/5016; C07F 15/0033; C09K 11/06; C09K 2211/1018; C09K 2211/1029; C09K 2211/1033; C09K 2211/1037; C09K 2211/104; C09K 2211/1088; C09K 2211/1092; C09K 2211/1096; C09K 2211/185
    USPC ............ 428/690, 691, 917; 427/58, 66; 313/500–512; 257/40, 88–104, 257/E51.001–E51.052; 252/301.16–301.35; 548/103, 108, 402; 546/4, 10
    See application file for complete search history.

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,692,241 B1 * | 4/2014 | Zeng et al. ............ 257/40 |
| 8,932,734 B2 * | 1/2015 | Dyatkin ............ 428/690 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0088167 A1 * | 4/2007 | Lin et al. ............ 548/103 |
| 2007/0190359 A1 * | 8/2007 | Knowles ............ C07F 15/0033 428/690 |
| 2007/0196691 A1 * | 8/2007 | Ikemizu et al. ............ 428/690 |
| 2007/0247061 A1 * | 10/2007 | Adamovich et al. ......... 313/504 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0233433 A1 * | 9/2008 | Igarashi et al. ............ 428/704 |
| 2008/0297033 A1 | 12/2008 | Knowles et al. |
| 2008/0297038 A1 * | 12/2008 | Yagi ............ C07F 15/0033 313/504 |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0187984 A1 * | 7/2010 | Lin et al. ............ 313/504 |
| 2011/0204333 A1 * | 8/2011 | Xia et al. ............ 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2008074939 A * | 4/2008 |
| JP | 2013235994 | 11/2013 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |

(56) References Cited

FOREIGN PATENT DOCUMENTS

| | | |
|---|---|---|
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | WO 2008044723 A1 * | 4/2008 ............ C09K 11/06 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | WO 2009021126 A2 * | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Oshiyama et al., machine translation of WO 2008/044723 A1, date of Japanese language document: Apr. 17, 2008, pp. 1-195.*

Morello et al., "Accurate prediction of emission energies with TD-DFT methods for platinum and iridium OLED materials", J Mol Model (2017) vol. 23, article 174, pp. 1-10. (Year: 2017).*

Tavasli et al., "Colour tuning from green to red by substituent effects in phosphorescent tris-cyclometalated iridium(III) complexes of carbazole-based ligands: synthetic, photophysical, computational and high efficiency OLED studies" Journal of Materials Chemistry (2012) vol. 22, pp. 6419-6428. (Year: 2012).*

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis (dimesitylboryl)-2,2'5",2"-terthiophene as a Novel Family of Electron-Transporting Amorphous Molecular Materials," J. Am. Chem. Soc., 120 (37):9714-9715 (1998).

(56) References Cited

OTHER PUBLICATIONS

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett, 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

PHOSPHORESCENT EMITTERS WITH PHENYLIMIDAZOLE LIGANDS

CROSS-REFERENCE TO RELATED APPLICATIONS

This application claims priority to U.S. Provisional Application Ser. No. 61/692,987, filed Aug. 24, 2012, the entire contents of which are incorporated herein by reference.

JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the invention relates to phosphorescent light emitting materials that may have improved stability when used in an OLED.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

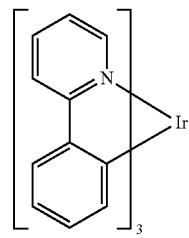

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A new type of light emitting material is provided. This new class of material includes compounds having a metal $M_1$ complexed to a ligand $L_3$ containing an azadibenzothiophene or an azadibenzofuran group, which is represented Formula (I), below:

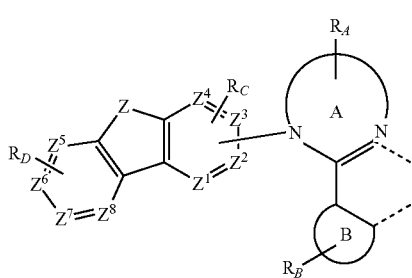

(I)

wherein A and B are each independently a 5-membered or 6-membered carbocyclic or heterocyclic ring; wherein $R_A$, $R_B$, $R_C$, and $R_D$ each represent mono, di, tri, tetra substitutions, or no substitution; wherein $Z^1$, $Z^2$, $Z^3$, $Z^4$, $Z^5$, $Z^6$, $Z^7$, and $Z^8$ are each selected from N or C; wherein at least one of $Z^1$, $Z^2$, $Z^3$, $Z^4$, $Z^5$, $Z^6$, $Z^7$, and $Z^8$ is N; wherein one of $Z^1$, $Z^2$, $Z^3$, and $Z^4$ is C that is bonded to N of A; wherein Z is selected from the group consisting of BR, NR, PR, O, S, Se, C=O, S=O, $SO_2$, CRR', SiRR', and GeRR'; wherein R, R', $R_A$, $R_B$, $R_C$, and $R_D$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein any two adjacent R, R', $R_A$, $R_B$, $R_C$, and $R_D$ are optionally joined to form a ring, which may be further substituted; and wherein $L_3$ may be linked with other ligands to comprise a, tridentate, tetradentate, pentadentate, or hexadentate ligand.

The compound can be homoleptic or heteroleptic. In some embodiments, the compound is homoleptic. In other embodiments, the compound is heteroleptic.

In some embodiments, the ring B is a phenyl ring, which can be substituted as indicated above.

The compound can include any suitable metal, $M_1$. In some embodiments, $M_1$ is Ir.

At least one of $Z^1$, $Z^2$, $Z^3$, $Z^4$, $Z^5$, $Z^6$, $Z^7$, and $Z^8$ is N. In some embodiments, only one of $Z^1$, $Z^2$, $Z^3$, $Z^4$, $Z^5$, $Z^6$, $Z^7$, and $Z^8$ is N. In some embodiments, $Z^1$ is N. In some further embodiments, $Z^2$ is N. In some further embodiments, $Z^3$ is N. In some further embodiments, $Z^4$ is N. In some further embodiments, $Z^5$ is N. In some further embodiments, $Z^6$ is N. In some further embodiments, $Z^7$ is N. In some further embodiments, $Z^8$ is N.

In some embodiments, $Z^1$ is bonded to N of ring A. In some such embodiments, $Z^2$ is CR", where R" is alkyl, cycloalkyl, aryl, or substituted aryl.

In some other embodiments, $Z^2$ is bonded to N of ring A. In some such embodiments, $Z^1$ and $Z^3$ are CR", where R" is alkyl, cycloalkyl, aryl, or substituted aryl.

In some embodiments, $Z^1$ is bonded to N of ring A. In some such embodiments, $Z^2$ is CR", where R" is alkyl, cycloalkyl, aryl, or substituted aryl.

In some embodiments, $Z^1$ is bonded to N of ring A. In some such embodiments, $Z^2$ is CR", where R" is alkyl, cycloalkyl, aryl, or substituted aryl.

In some further embodiments of any of the foregoing embodiments, R" is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, and combinations thereof.

In some embodiments, Z is O or S.

In some embodiments, the ligand $L_3$ is a ligand having Formula (II):

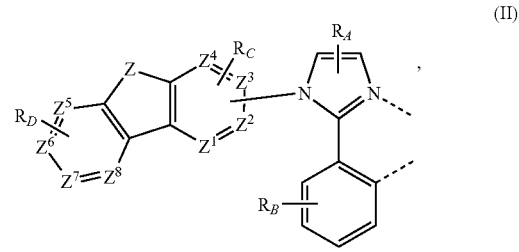

(II)

where the variables have the meanings as defined above.

In some embodiments, the coordination compound if a compound having Formula (III):

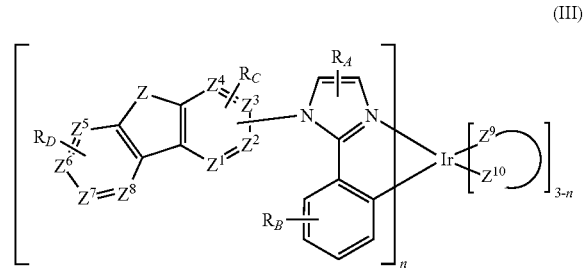

(III)

where $Z^9$-$Z^{10}$ is a bidentate ligand; n is 1, 2, or 3; and the other variables have the definitions provided above. In some such embodiments, $Z^9$-$Z^{10}$ is 2-phenylimidazole, 1-phenylimidazole, 2-phenylpyridyl, 1-(4-dibenzofuran)imidazole, or 1-(4-dibenzothiophene)imidazole, each of which is optionally substituted one or more times by substituents selected independently from the group consisting of alkyl, cycloalkyl, aryl, heteroaryl, and combinations thereof.

In some embodiments, the coordination compound is a compound selected from the group consisting of:

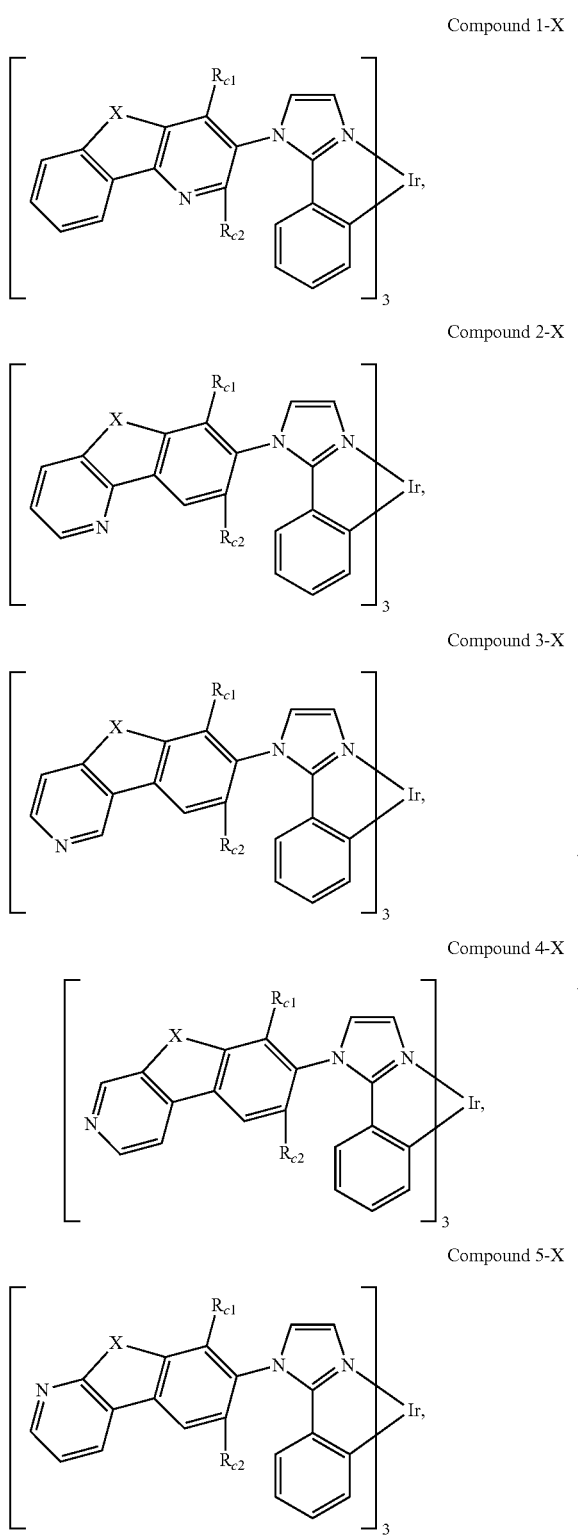

Compound 1-X

Compound 2-X

Compound 3-X

Compound 4-X

Compound 5-X

-continued

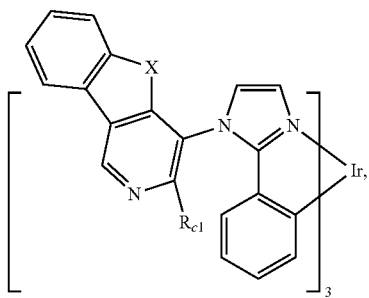

Compound 6-X

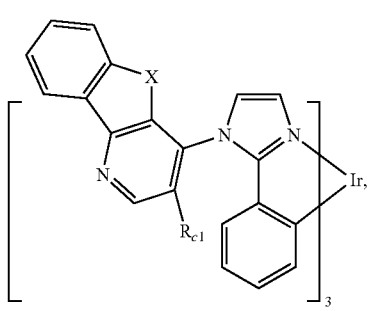

Compound 7-X

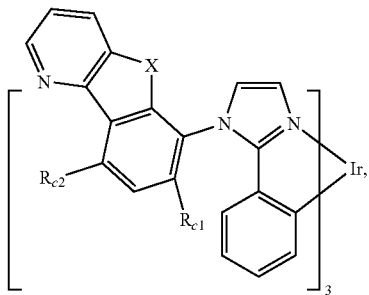

Compound 8-X

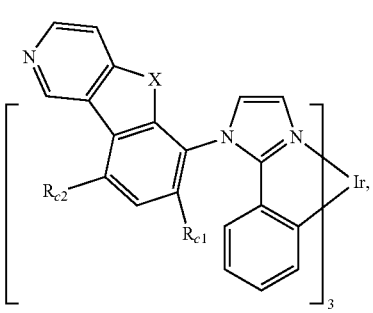

Compound 9-X

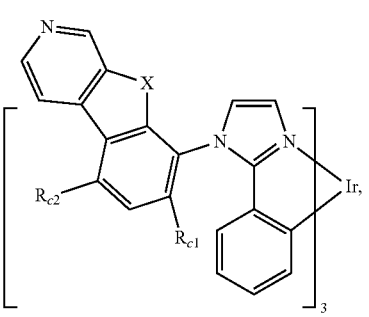

Compound 10-X

Compound 11-X
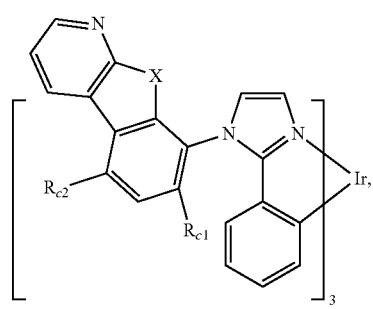
Compound 12-X
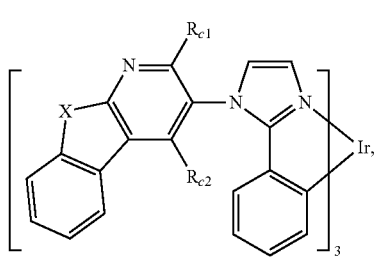
Compound 13-X
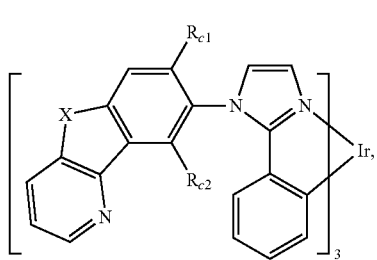
Compound 14-X
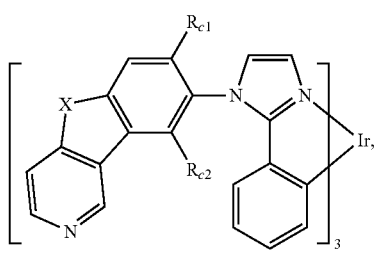
Compound 15-X
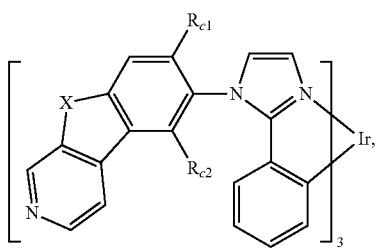
Compound 16-X
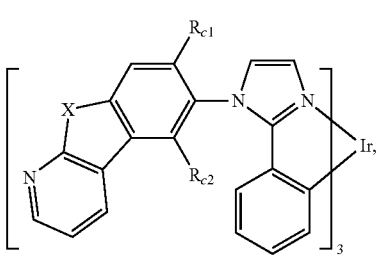
Compound 17-X
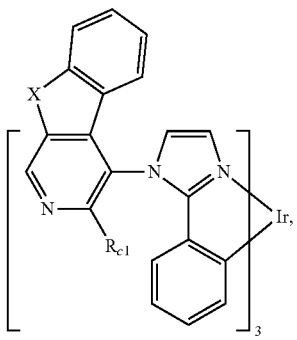
Compound 18-X
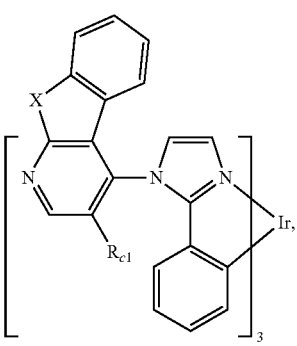
Compound 19-X
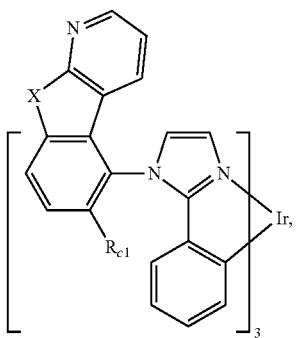
Compound 20-X
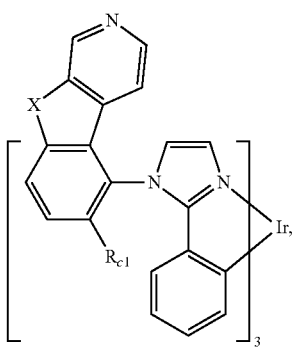

Compound 21-X
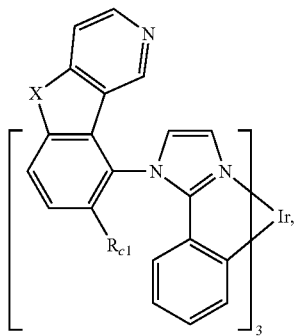
Compound 22-X
Compound 26-X
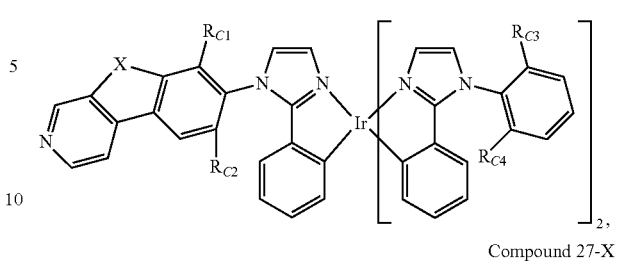
Compound 27-X
Compound 28-X
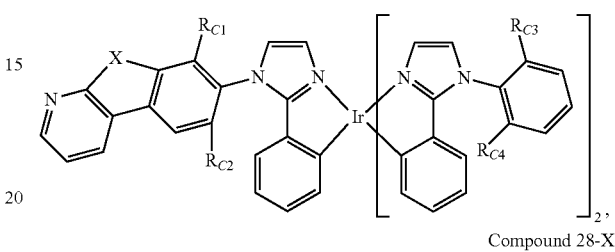
Compound 29-X
Compound 30-X
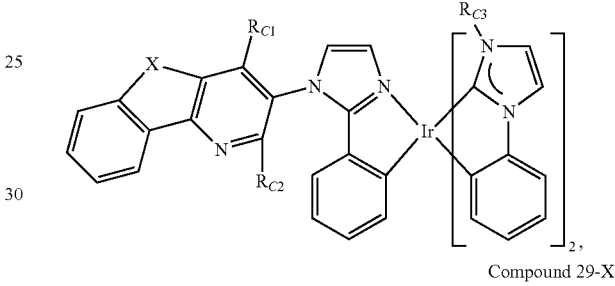
Compound 31-X
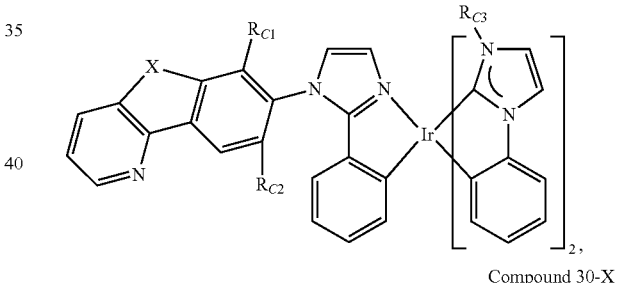
Compound 23-X
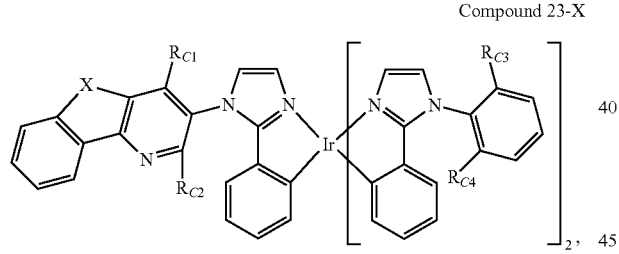
Compound 24-X
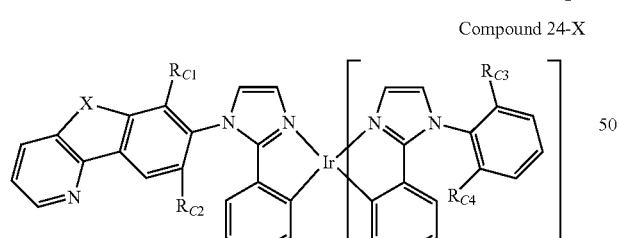
Compound 25-X
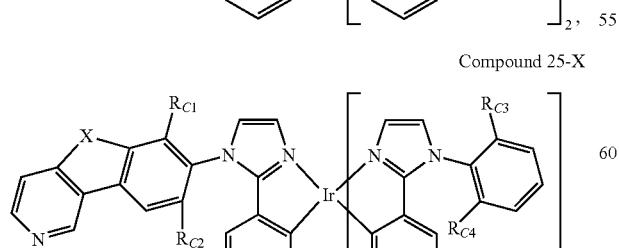

Compound 32-X
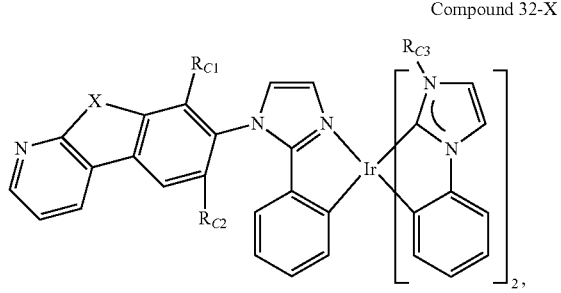
Compound 37-X
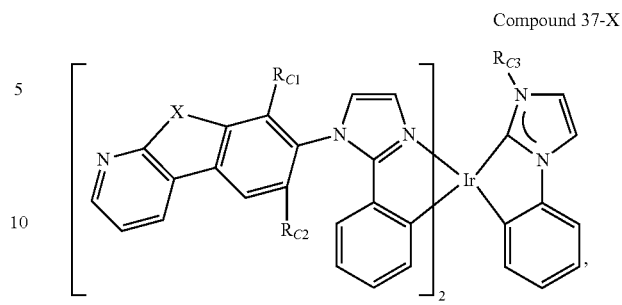
Compound 33-X
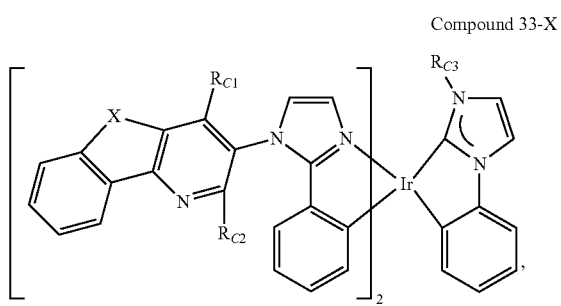
Compound 38-X
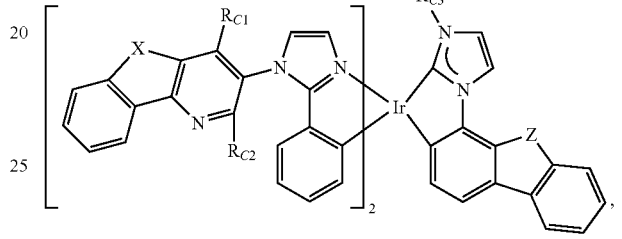
Compound 34-X
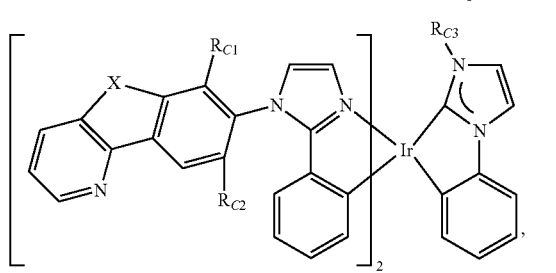
Compound 39-X
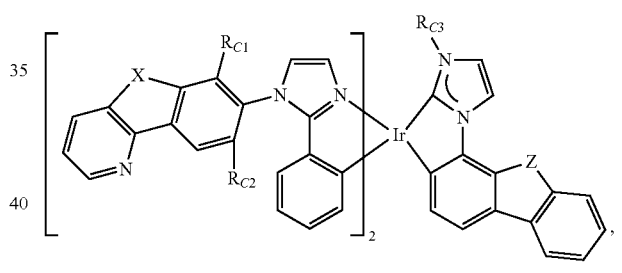
Compound 35-X
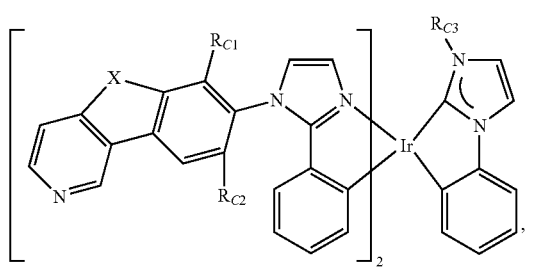
Compound 40-X
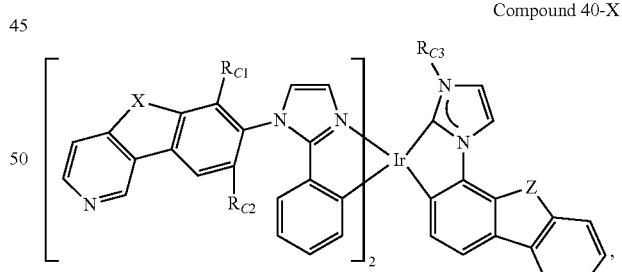
Compound 36-X
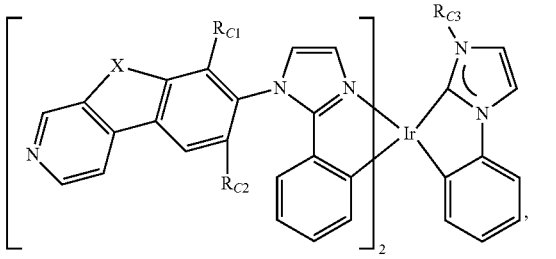
Compound 41-X
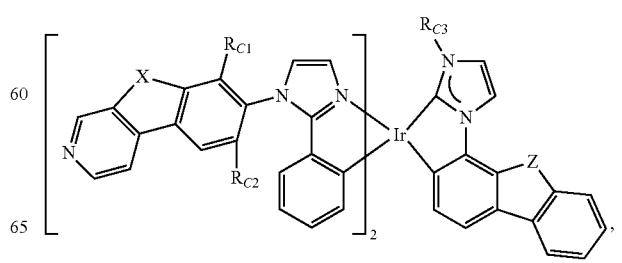

Compound 42-X

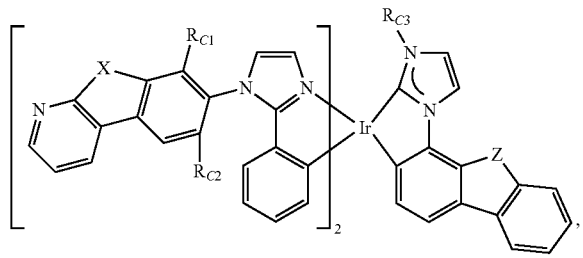

Compound 43-X

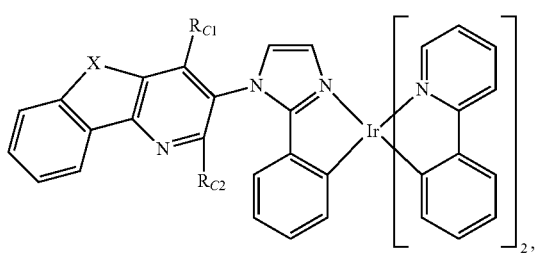

Compound 44-X

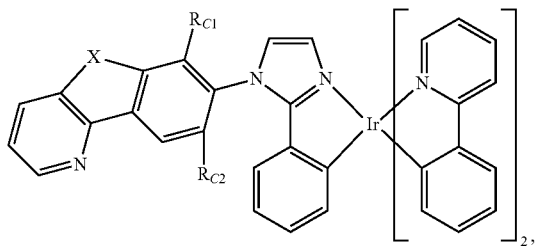

Compound 45-X

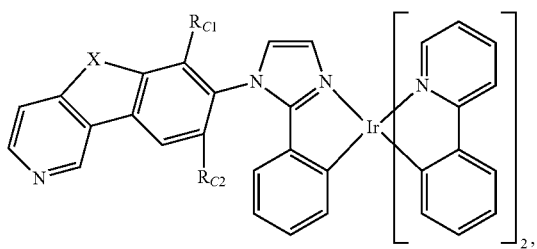

Compound 46-X

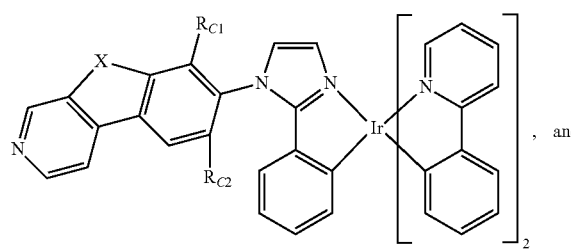

Compound 47-X

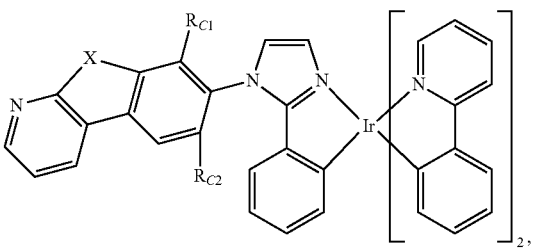

wherein $R_{C1}$, $R_{C2}$, $R_{C3}$ and $R_{C4}$ are each independently selected from the group consisting of alkyl, cycloalkyl, aryl, heteroaryl, and combinations thereof; and X and Z are O or S.

In some such embodiments, $R_{C1}$, $R_{C2}$, $R_{C3}$ and $R_{C4}$ are each independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof; and wherein any group is optionally partially or fully deuterated.

In some further embodiments, the coordination compound is a compound selected from the group consisting of:

Compound 1-O-1

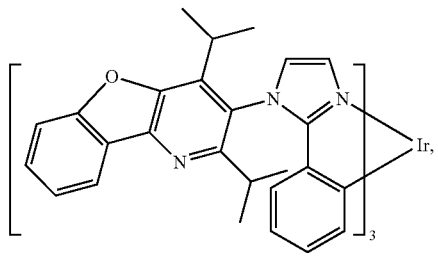

Compound 2-O-1

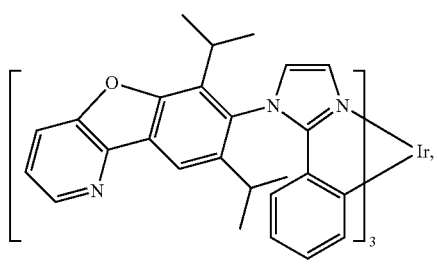

Compound 3-O-1

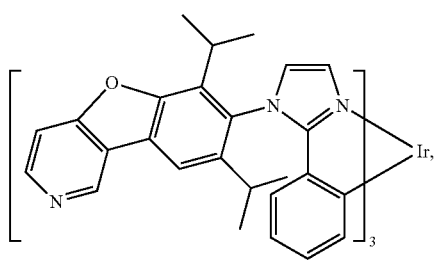

-continued

Compound 4-O-1

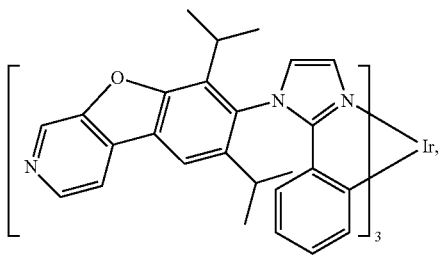

Compound 5-O-1

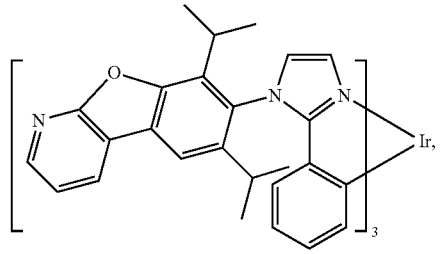

Compound 1-S-1

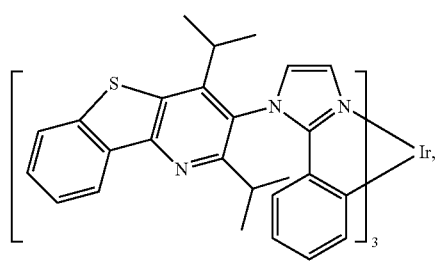

Compound 2-S-1

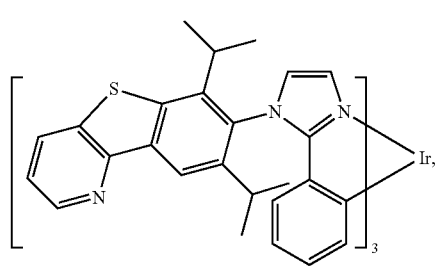

Compound 3-S-1

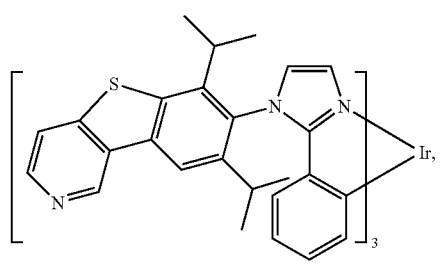

-continued

Compound 4-S-1

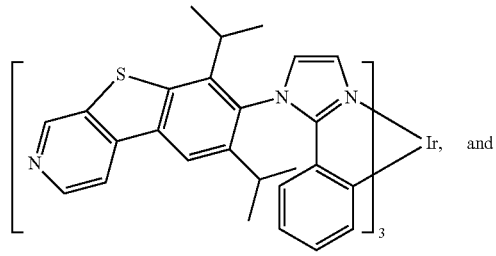 and

Compound 5-S-1

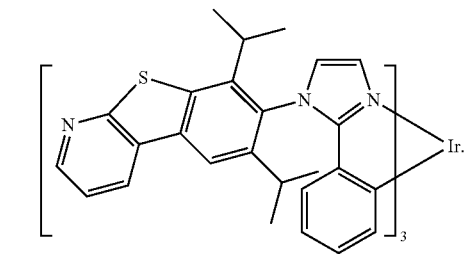

Devices are also provided. In some embodiments, a first device is provided, which comprises a first light emitting device, which further comprises: an anode; a cathode; and an organic layer disposed between the anode and the cathode, which comprises a coordination compound of any of the above embodiments. In some embodiments, the first device is a consumer product. In some embodiments, the first device is an organic light emitting device. In some embodiments, the device comprises a lighting panel.

In some embodiments, the organic layer in the device is an emissive layer. In some such embodiments, the coordination compound is an emissive dopant. In other such embodiments, the coordination compound is a non-emissive dopant.

In some embodiments, the organic layer in the device further comprises a host. Any suitable host can be used. In some embodiments, the host comprises a triphenylene containing benzo-fused thiophene or benzo-fused furan; wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution; wherein n is from 1 to 10; and wherein $Ar_1$ and $Ar_2$ are independently selected from the group consisting of benzene, biphenyl, naphthalene, triphenylene, carbazole, and heteroaromatic analogs thereof. In some embodiments, the host comprises a compound selected from the group consisting of: carbazole, dibenzothiphene, dibenzofuran, dibenzoselenophene, azacarbazole, aza-dibenzothiophene, aza-dibenzofuran, and aza-dibenzoselenophene.

In some further such embodiments, the host is a compound selected from the group consisting of:

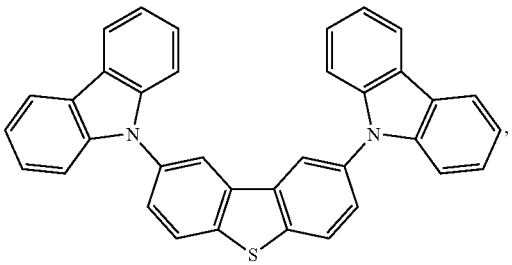

-continued

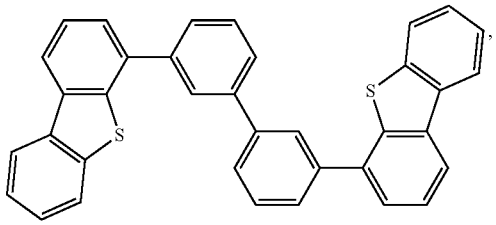
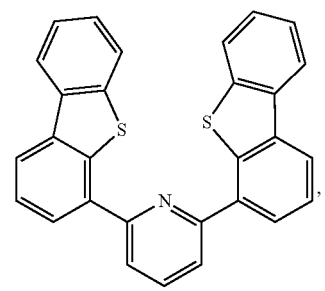
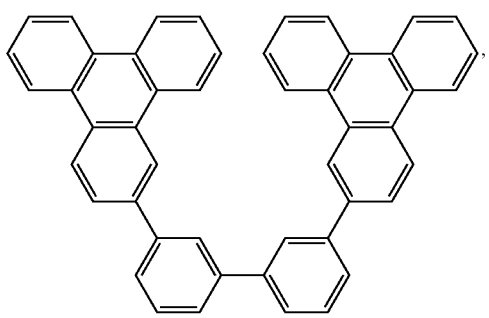
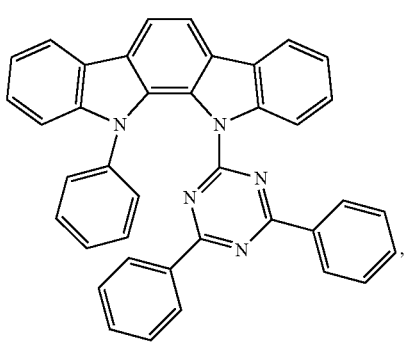
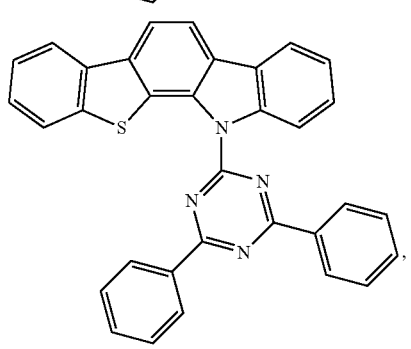

-continued

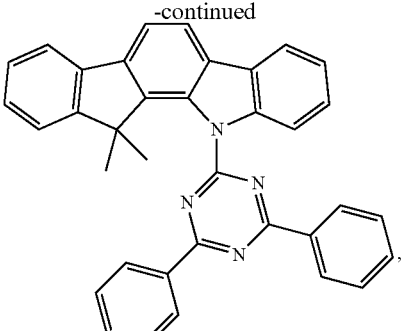
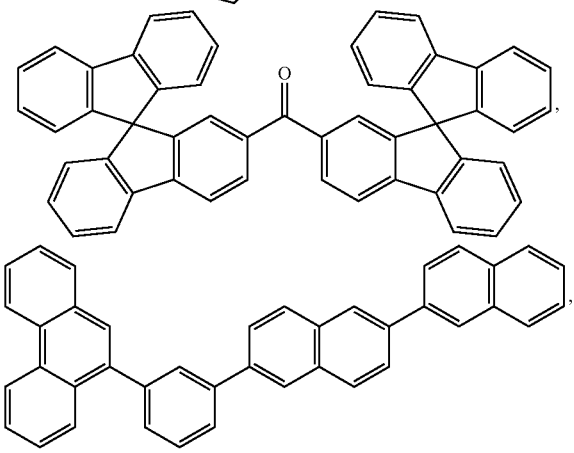
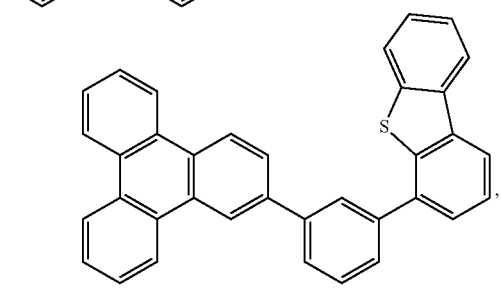
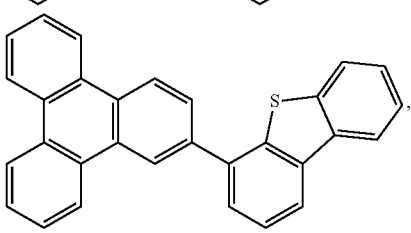

and combinations thereof.

In some embodiments, the host comprises a metal complex.

Other embodiments and aspects of the invention are described in further detail below.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
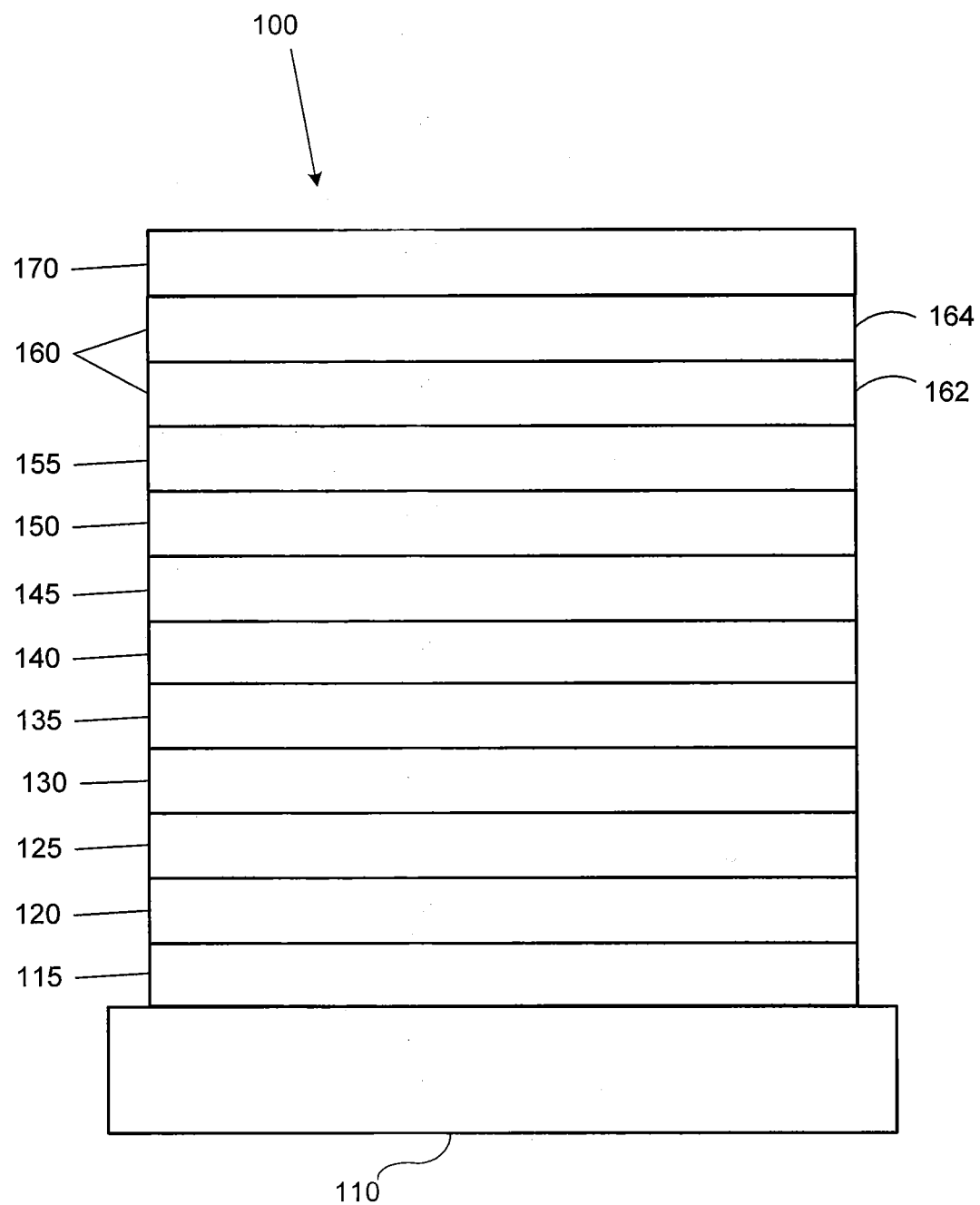
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
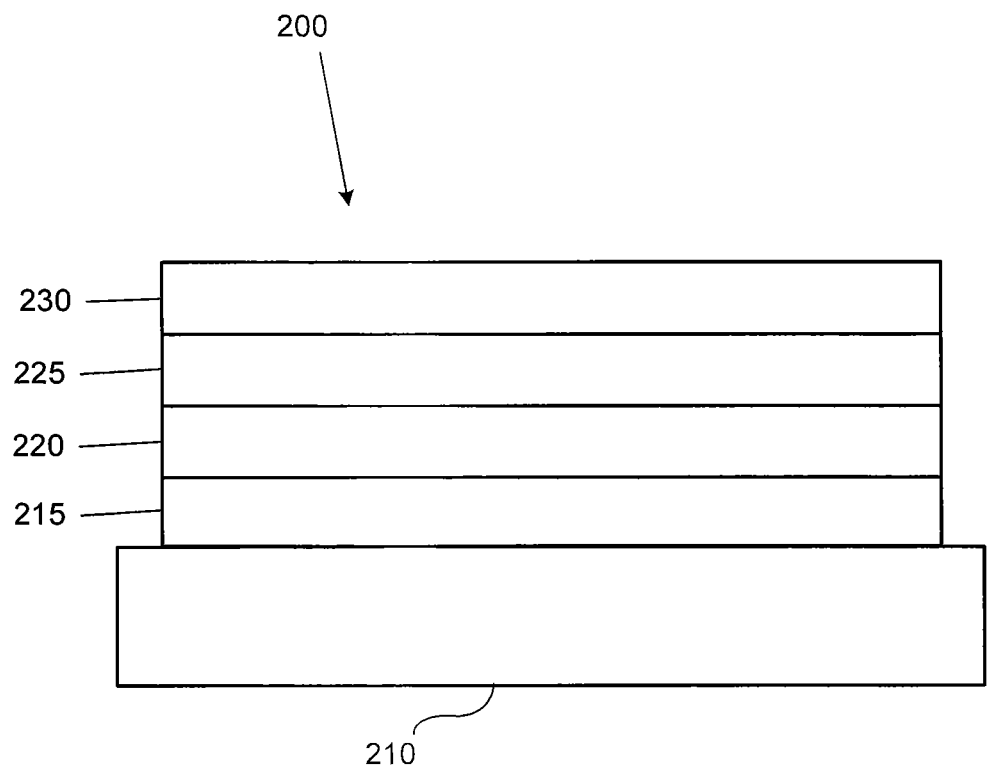
FIG. 2 shows an inverted organic light emitting device that does not have a separate electron transport layer.
Figure 3:
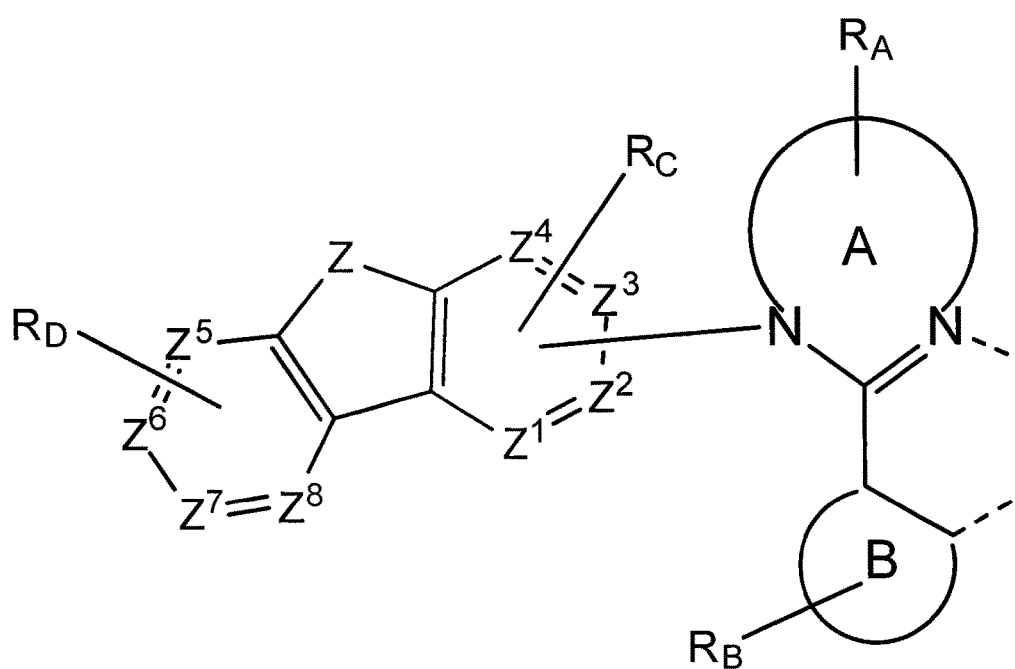
FIG. 3 shows a ligand $L_3$, which can be coordinated to a metal.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser.

No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Iridium complexes having phenylimidazole ligands with a twisted ring substituent on the imidazole can exhibit improved sublimation properties, and can improve the device stability when used in a phosphorescent organic light-emitting device (PHOLED). Such twisted ring substituents can include bulky substituents in positions immediately adjacent to where the ring bonds to the imidazole. By placing bulky groups in these positions, the ring substituent twists, thereby disrupting the conjugation. Moreover, steric effects created by these bulky groups can slow down the degradation of the complex by oxygen. In such twisted aryl compounds, the LUMO is generally localized on the ring substituent. Increasing the conjugation of the ring substituent can improve device stability. For example, the ring substituent can include groups such as dibenzofuran or dibenzothiophene.

Azadibenzofuran and azadibenzothiophene can be used as host materials in OLEDs. The inclusion of the nitrogen in the ring tends to lower LUMO with respect to dibenzofuran and dibenzothiophene. Thus, such nitrogen-substituted rings are more electron friendly when used in a device and, because of the lower LUMO, have greater device stability. Aryl-substituted phenylimidazole coordination compounds have a LUMO that is generally localized on the aryl substituent that is bonded to the imidazole. Therefore, device stability may be improved by modifying the aryl substituents in a manner so as to lower the LUMO. However, lowering the LUMO can change certain photophysical properties of the complex, and may cause its emission to shift toward the red, thereby making the compound undesirable for use as a blue emitter. Coordination compounds having an azadibenzofuran- or azadibenzothiophene-substituted phenylimidazole ligand are provided herein. The use of azadibenzofuran and azadibenzothiophene substituents resulted in a singlet energy that is shifted toward red in comparison to comparable dibenzofuran- or dibenzothiophene-substituted compounds. However, the compounds exhibited only a negligible shift of the triplet. Thus, substituting the phenylimidazole ligand with azadibenzofuran or azadibenzothiophene can lead to compounds having improved device stability, which can still function as a blue emitter.

The "aza" designation in the fragments described above, i.e. azadibenzofuran, azadibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

A new type of light emitting material is provided. This new class of material includes compounds having a metal $M_1$ complexed to a ligand $L_3$ containing an azadibenzothiophene or an azadibenzofuran group, which is represented Formula (I), below:

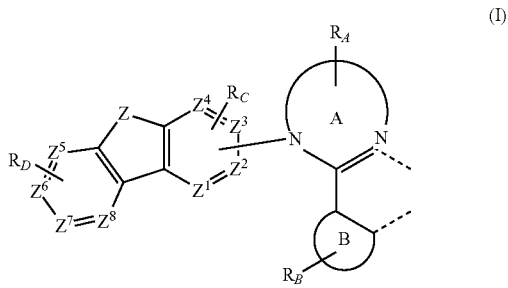

wherein A and B are each independently a 5-membered or 6-membered carbocyclic or heterocyclic ring; wherein $R_A$, $R_B$, $R_C$, and $R_D$ each represent mono, di, tri, tetra substitutions, or no substitution; wherein $Z^1$, $Z^2$, $Z^3$, $Z^4$, $Z^5$, $Z^6$, $Z^7$, and $Z^8$ are each selected from N or C; wherein at least one of $Z^1$, $Z^2$, $Z^3$, $Z^4$, $Z^5$, $Z^6$, $Z^7$, and $Z^8$ is N; wherein one of $Z^1$, $Z^2$, $Z^3$, and $Z^4$ is C that is bonded to N of A; wherein Z is selected from the group consisting of BR, NR, PR, O, S, Se, C=O, S=O, SO$_2$, CRR', SiRR', and GeRR'; wherein R, R', $R_A$, $R_B$, $R_C$, and $R_D$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein any two adjacent R, R', $R_A$, $R_B$, $R_C$, and $R_D$ are optionally joined to form a ring, which may be further substituted; and wherein $L_3$ may be linked with other ligands to comprise a, tridentate, tetradentate, pentadentate, or hexadentate ligand.

The compound can be homoleptic or heteroleptic. In some embodiments, the compound is homoleptic. In other embodiments, the compound is heteroleptic.

In some embodiments, the ring B is a phenyl ring, which can be substituted as indicated above.

The compound can include any suitable metal, $M_1$. In some embodiments, $M_1$ is Ir.

At least one of $Z^1$, $Z^2$, $Z^3$, $Z^4$, $Z^5$, $Z^6$, $Z^7$, and $Z^8$ is N. In some embodiments, only one of $Z^1$, $Z^2$, $Z^3$, $Z^4$, $Z^5$, $Z^6$, $Z^7$, and $Z^8$ is N. In some embodiments, $Z^1$ is N. In some further embodiments, $Z^2$ is N. In some further embodiments, $Z^3$ is N. In some further embodiments, $Z^4$ is N. In some further embodiments, $Z^5$ is N. In some further embodiments, $Z^6$ is N. In some further embodiments, $Z^7$ is N. In some further embodiments, $Z^8$ is N.

In some embodiments, $Z^1$ is bonded to N of ring A. In some such embodiments, $Z^2$ is CR", where R" is alkyl, cycloalkyl, aryl, or substituted aryl.

In some other embodiments, $Z^2$ is bonded to N of ring A. In some such embodiments, $Z^1$ and $Z^3$ are CR", where R" is alkyl, cycloalkyl, aryl, or substituted aryl.

In some embodiments, $Z^1$ is bonded to N of ring A. In some such embodiments, $Z^2$ is CR", where R" is alkyl, cycloalkyl, aryl, or substituted aryl.

In some embodiments, $Z^1$ is bonded to N of ring A. In some such embodiments, $Z^2$ is CR", where R" is alkyl, cycloalkyl, aryl, or substituted aryl.

In some further embodiments of any of the foregoing embodiments, R" is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, and combinations thereof.

In some embodiments, Z is O or S.

In some embodiments, the ligand $L_3$ is a ligand having Formula (II):

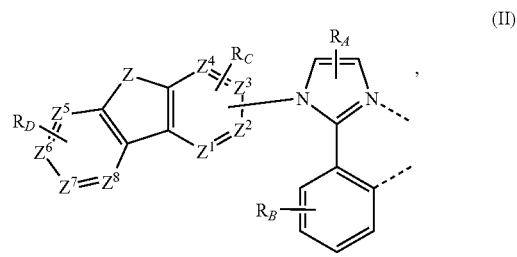

where the variables have the meanings as defined above.

In some embodiments, the coordination compound if a compound having Formula (III):

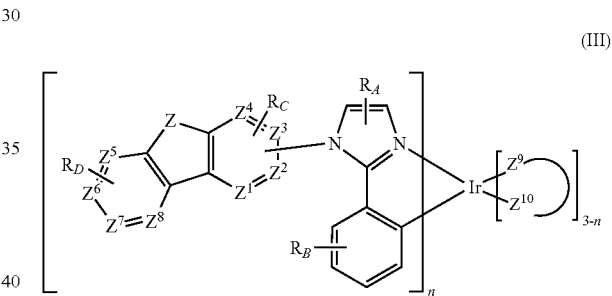

where $Z^9$-$Z^{10}$ is a bidentate ligand; n is 1, 2, or 3; and the other variables have the definitions provided above. In some such embodiments, $Z^9$-$Z^{10}$ is 2-phenylimidazole, 1-phenylimidazole, 2-phenylpyridyl, 1-(4-dibenzofuran)imidazole, or 1-(4-dibenzothiophene)imidazole, each of which is optionally substituted one or more times by substituents selected independently from the group consisting of alkyl, cycloalkyl, aryl, heteroaryl, and combinations thereof.

In some embodiments, the coordination compound is a compound selected from the group consisting of:

Compound 1-X

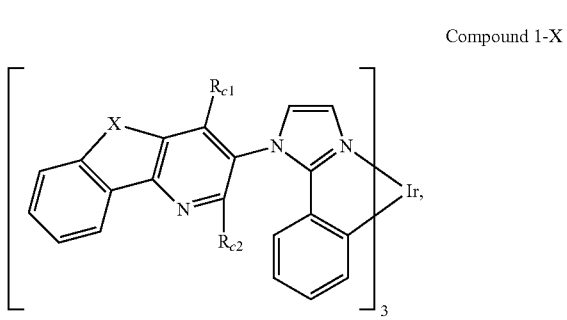

Compound 2-X
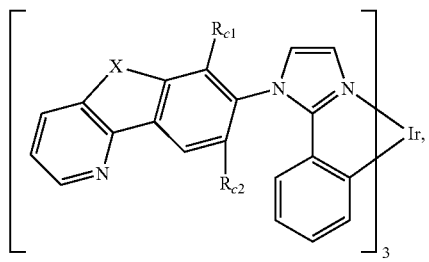
Compound 3-X
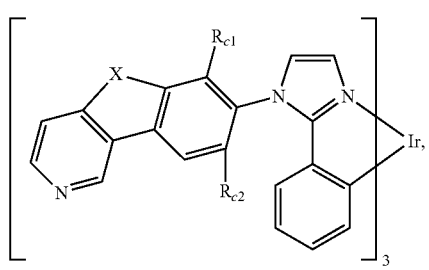
Compound 4-X
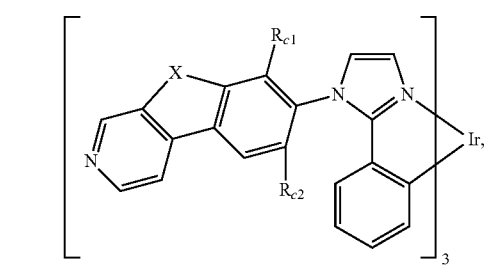
Compound 5-X
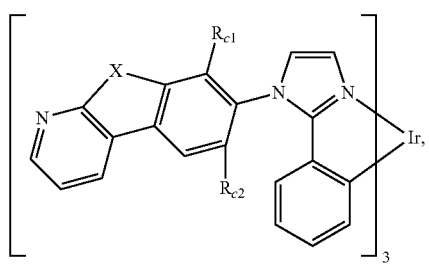
Compound 6-X
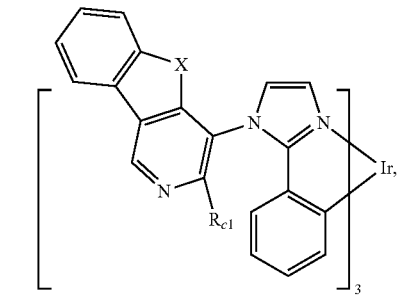
Compound 7-X
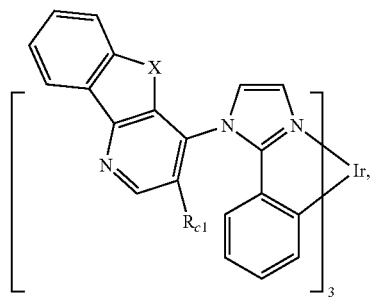
Compound 8-X
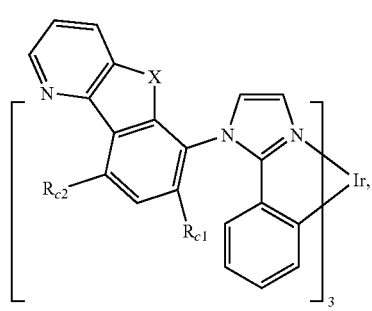
Compound 9-X
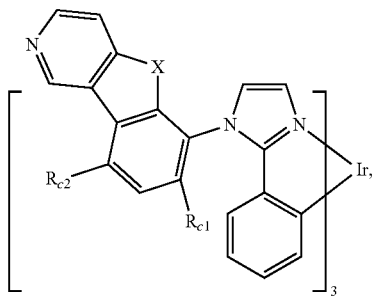
Compound 10-X
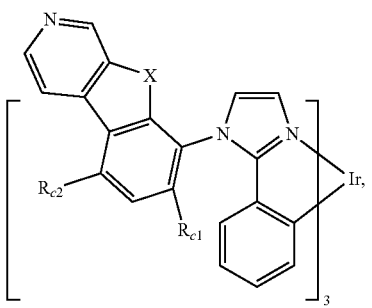
Compound 11-X
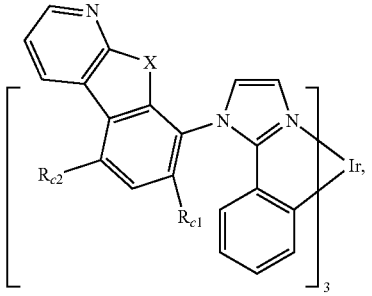

Compound 12-X
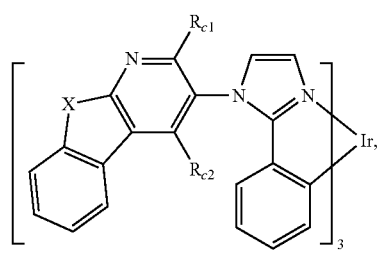
Compound 13-X
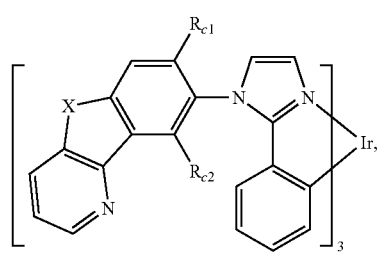
Compound 14-X
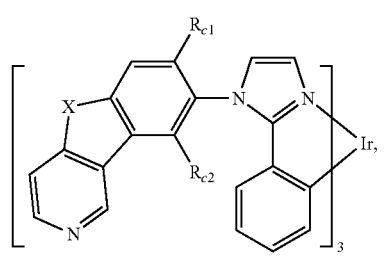
Compound 15-X
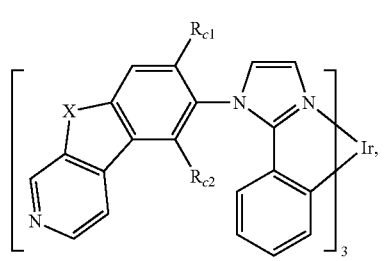
Compound 16-X
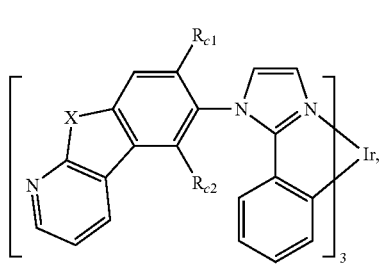
Compound 17-X
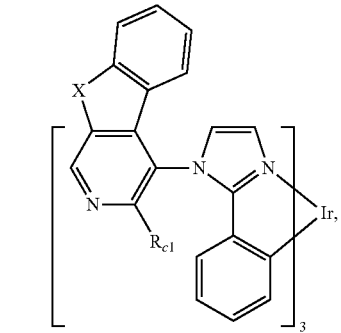
Compound 18-X
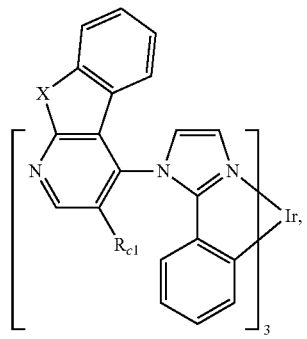
Compound 19-X
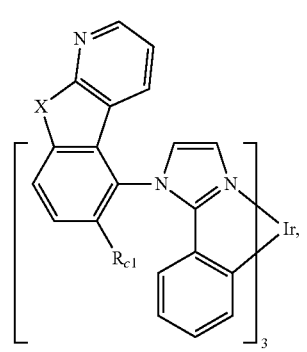
Compound 20-X
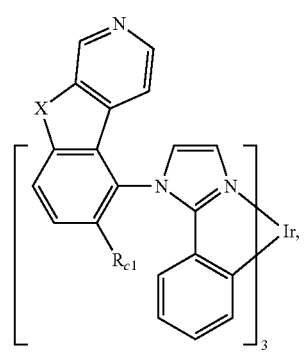
Compound 21-X
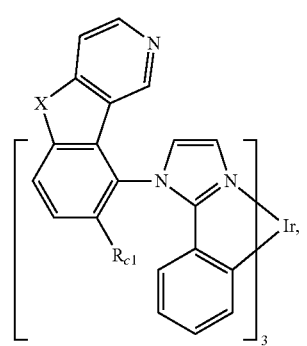

Compound 22-X
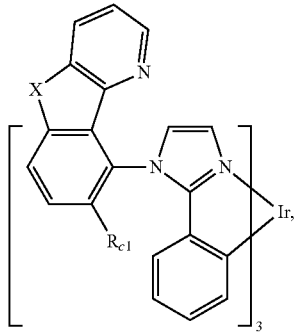
Compound 23-X
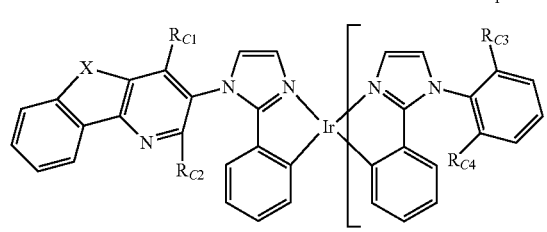
Compound 24-X
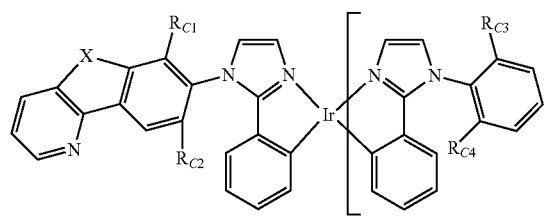
Compound 25-X
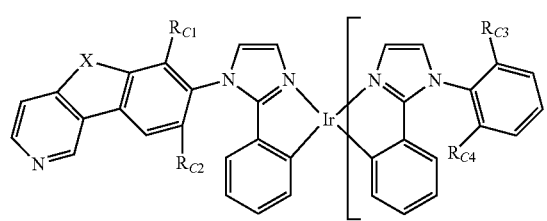
Compound 26-X
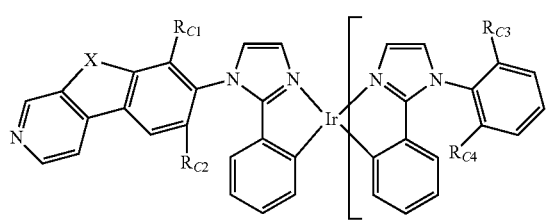
Compound 27-X
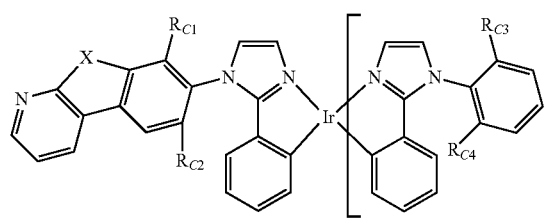
Compound 28-X
Compound 29-X
Compound 30-X
Compound 31-X
Compound 32-X
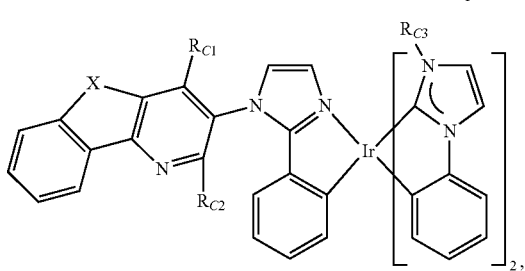

Compound 33-X
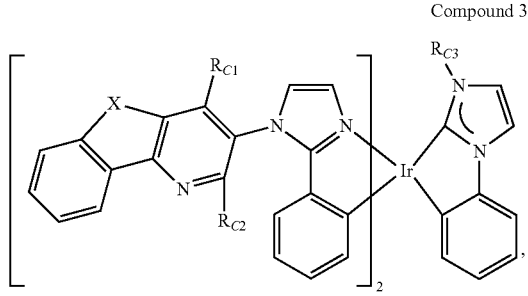
Compound 38-X
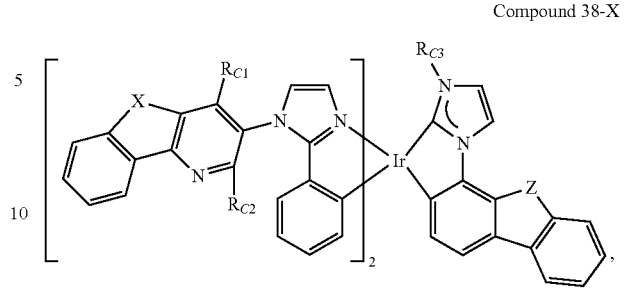
Compound 34-X
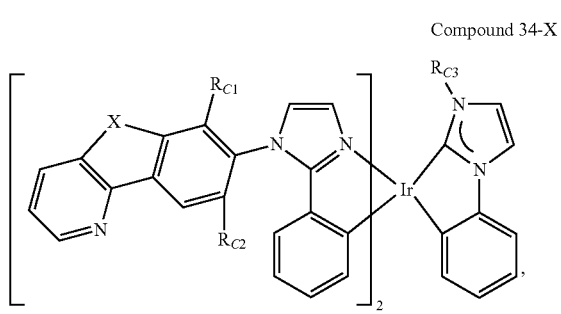
Compound 39-X
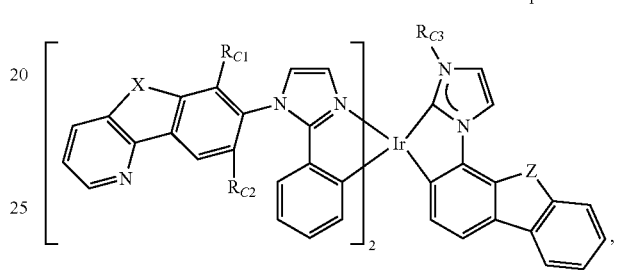
Compound 35-X
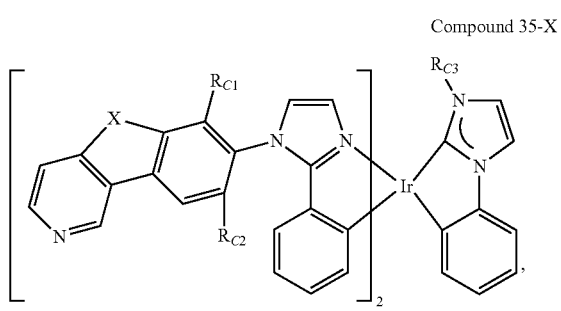
Compound 40-X
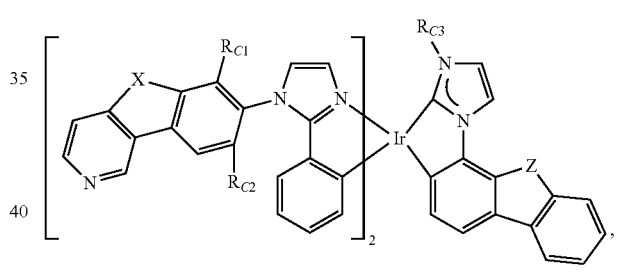
Compound 36-X
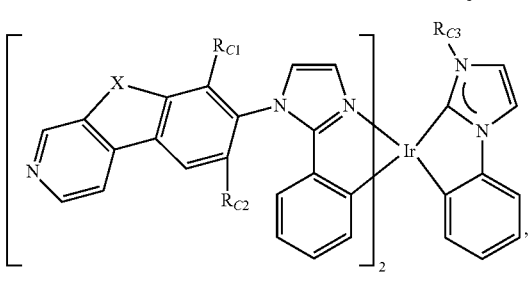
Compound 41-X
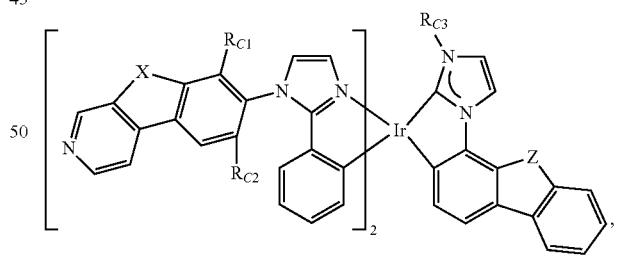
Compound 37-X
Compound 42-X
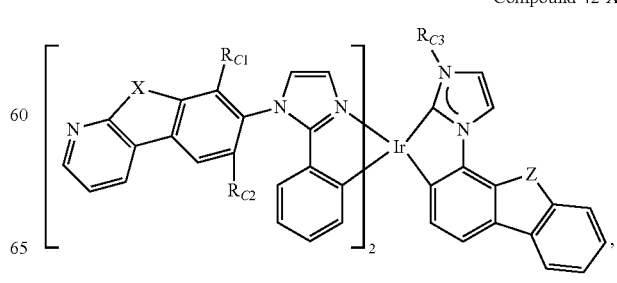

-continued

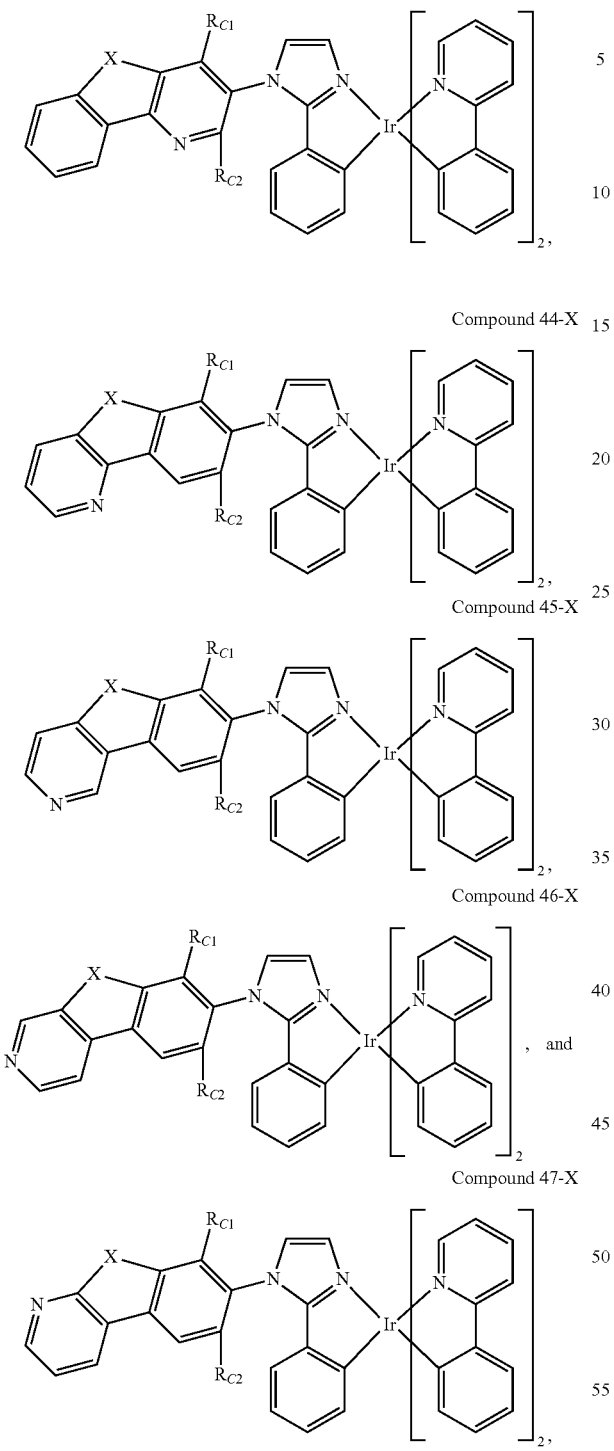

Compound 43-X

Compound 44-X

Compound 45-X

Compound 46-X

Compound 47-X wherein $R_{C1}$, $R_{C2}$, $R_{C3}$ and $R_{C4}$ are each independently selected from the group consisting of alkyl, cycloalkyl, aryl, heteroaryl, and combinations thereof; and Z and X are O or S.

In some such embodiments, $R_{C1}$, $R_{C2}$, $R_{C3}$ and $R_{C4}$ are each independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof; and wherein any group is optionally partially or fully deuterated.

In some further embodiments, the coordination compound is a compound selected from the group consisting of:

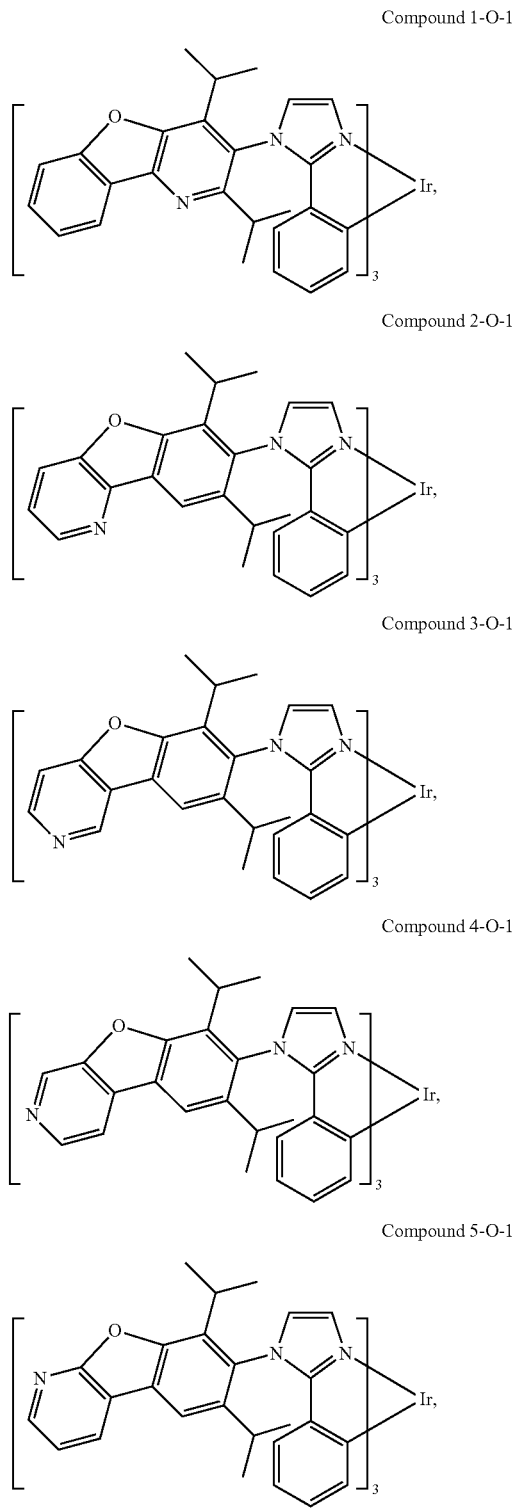

Compound 1-O-1

Compound 2-O-1

Compound 3-O-1

Compound 4-O-1

Compound 5-O-1

-continued

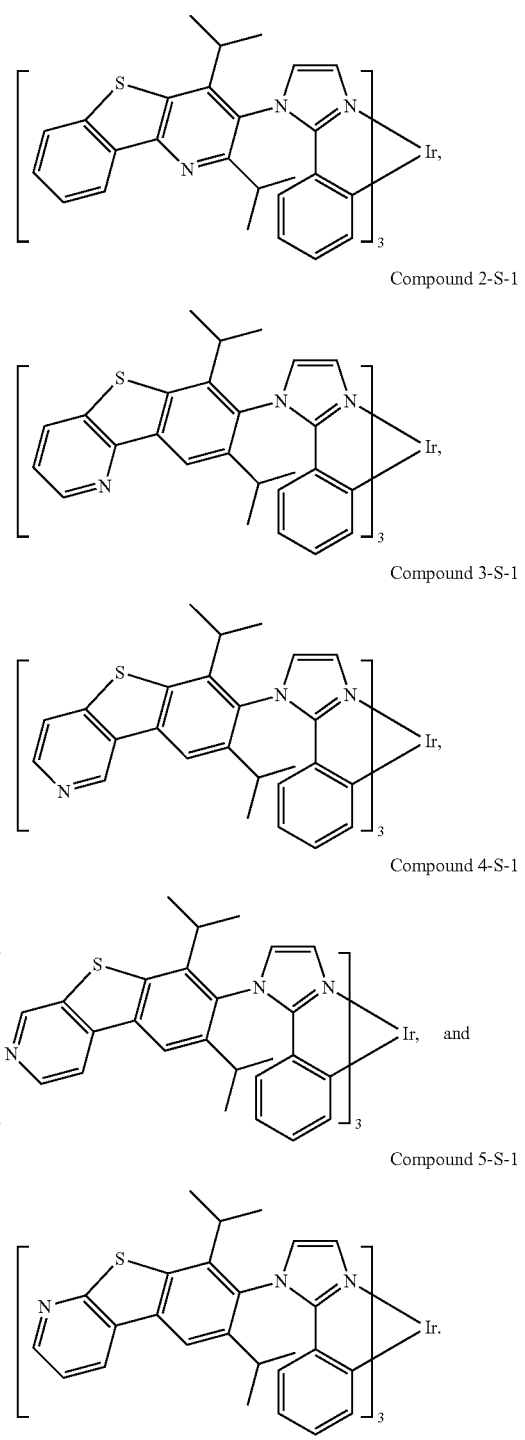

Compound 1-S-1

Compound 2-S-1

Compound 3-S-1

Compound 4-S-1

Compound 5-S-1

Devices are also provided. In some embodiments, a first device is provided, which comprises a first light emitting device, which further comprises: an anode; a cathode; and an organic layer disposed between the anode and the cathode, which comprises a coordination compound of any of the above embodiments. In some embodiments, the first device is a consumer product. In some embodiments, the first device is an organic light emitting device. In some embodiments, the device comprises a lighting panel.

In some embodiments, the organic layer in the device is an emissive layer. In some such embodiments, the coordination compound is an emissive dopant. In other such embodiments, the coordination compound is a non-emissive dopant.

In some embodiments, the organic layer in the device further comprises a host. Any suitable host can be used. In some embodiments, the host comprises a triphenylene containing benzo-fused thiophene or benzo-fused furan; wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-CH-C_{2n+1}$, $C\equiv CHC_nH_{2n+1}$, $Ar_1$, $Ar_1-Ar_2$, $C_nH_{2n}-Ar_1$, or no substitution; wherein n is from 1 to 10; and wherein $Ar_1$ and $Ar_2$ are independently selected from the group consisting of benzene, biphenyl, naphthalene, triphenylene, carbazole, and heteroaromatic analogs thereof. In some embodiments, the host comprises a compound selected from the group consisting of: carbazole, dibenzothiphene, dibenzofuran, dibenzoselenophene, azacarbazole, aza-dibenzothiophene, aza-dibenzofuran, and aza-dibenzoselenophene.

In some further such embodiments, the host is a compound selected from the group consisting of:

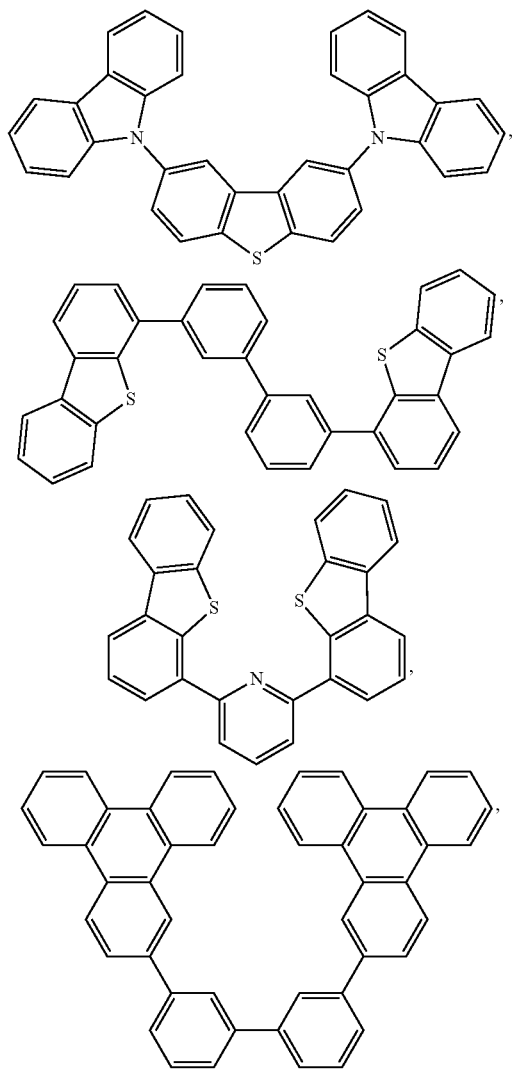

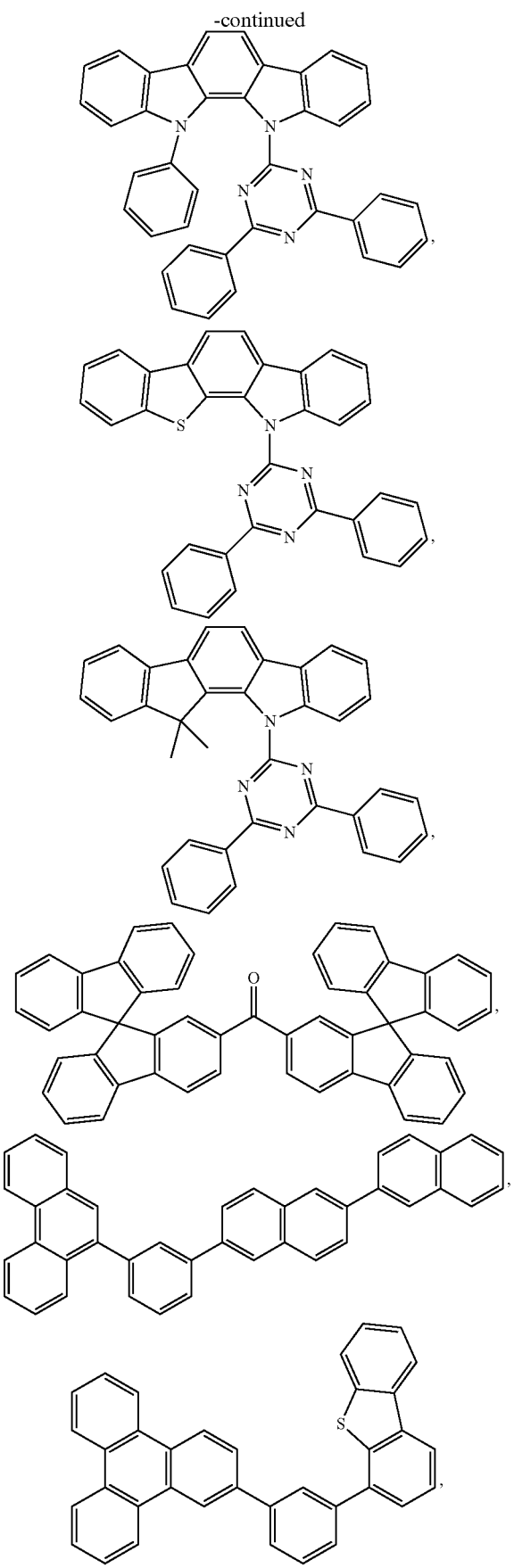

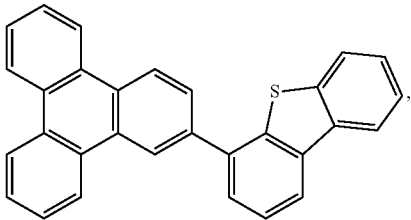 [SMILES: c1ccc2c(c1)sc1c(-c3ccc4c5ccccc5c5ccccc5c4c3)cccc12]

and combinations thereof.

In some embodiments, the host comprises a metal complex.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

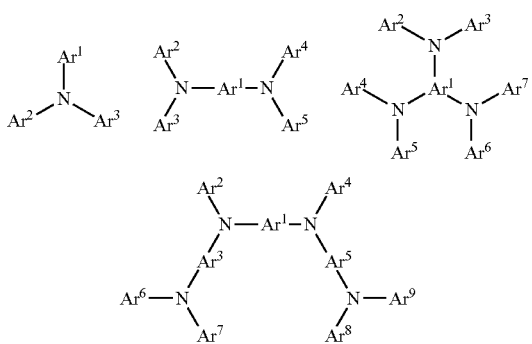

-continued

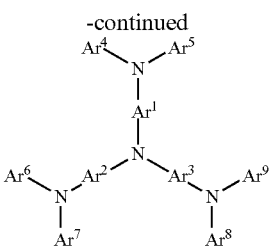

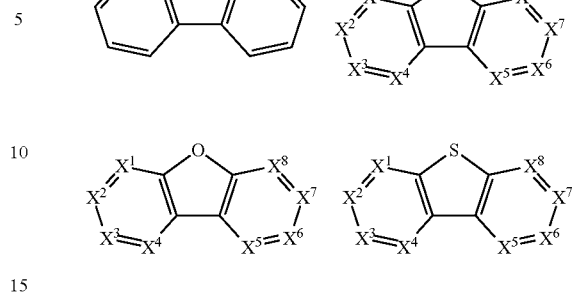

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

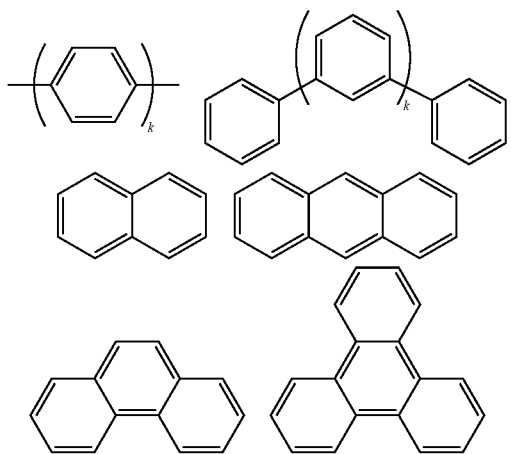

k is an integer from 1 to 20; $X^1$ to $X^8$ is C (including CH) or N; $Ar^1$ has the same group defined above.

Examples of metal complexes used in HIL or HTL include, but not limit to the following general formula:

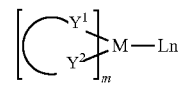

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

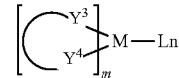

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

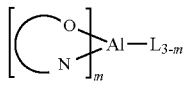 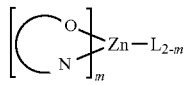

(O—N) is a bidentate ligand, having metal coordinated to atoms O and N.

In another aspect, M is selected from Ir and Pt.

In a further aspect, ($Y^3$-$Y^4$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

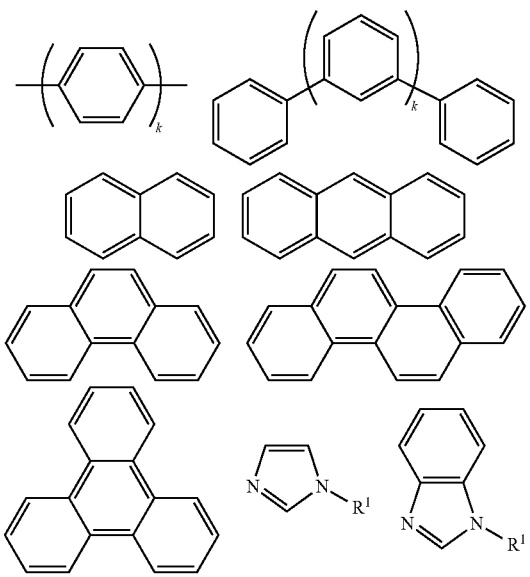

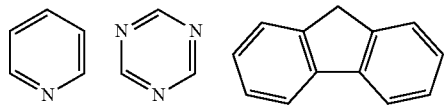

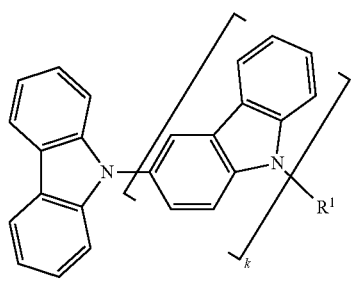

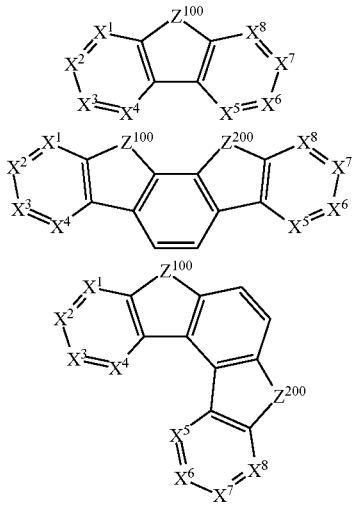

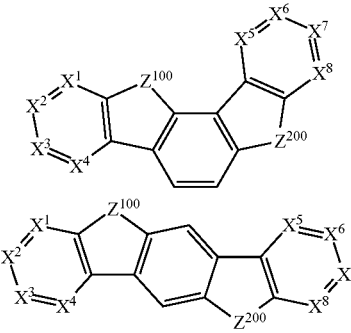

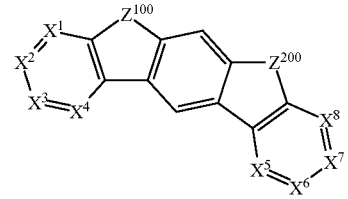

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

$Z^{100}$ and $Z^{200}$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

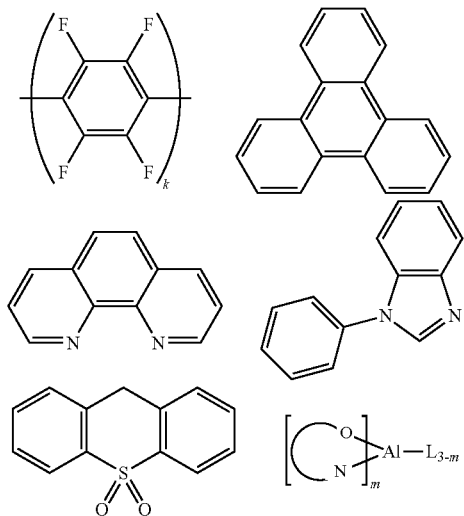

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

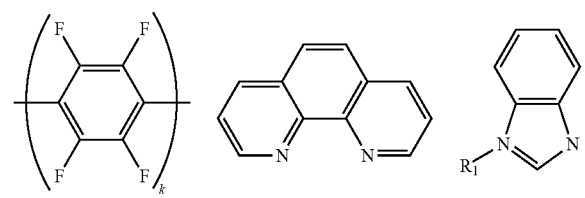

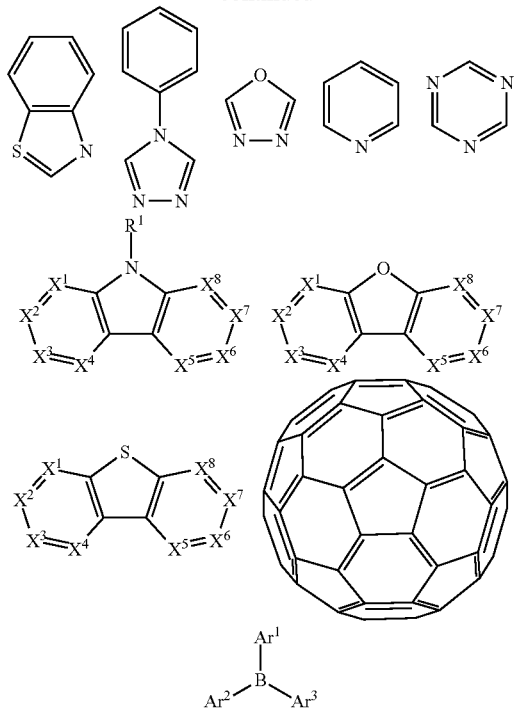

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

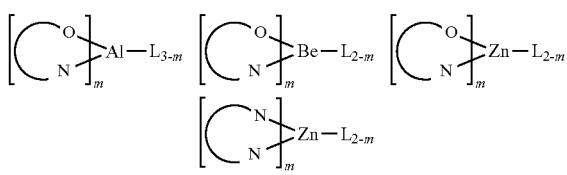

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED.

Non-limiting examples of the materials that may be used in an OLED in combination with materials disclosed herein are listed in Table I below. Table I lists non-limiting classes of materials, non-limiting examples of compounds for each class, and references that disclose the materials.

TABLE I

| MATERIAL | EXAMPLES OF MATERIAL | PUBLICATIONS |
|---|---|---|
| Hole injection materials | | |
| Phthalocyanine and porphryin compounds | 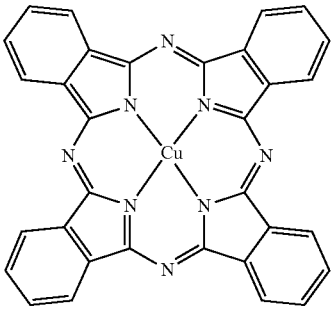 | Appl. Phys. Lett. 69, 2160 (1996) |
| Starburst triarylamines | 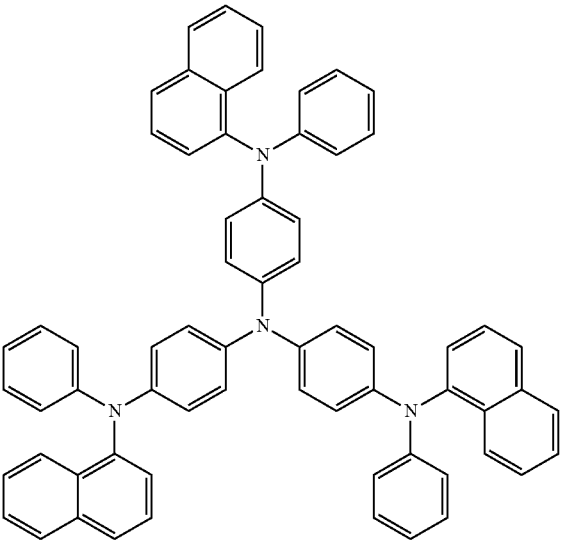 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-\!\!\left[CH_xF_y\right]_{\overline{n}}\!\!-$ | Appl. Phys. Lett. 78, 673 (2001) |
| Conducting polymers (e.g., PEDOT:PSS, polyaniline, polypthiophene) | 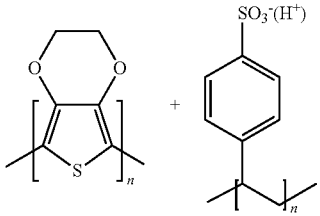 | Synth. Met. 87, 171 (1997) WO2007002683 |
| Phosphonic acid and sliane SAMs | 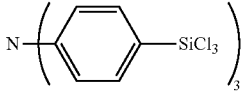 | US20030162053 |

TABLE I-continued
| MATERIAL | EXAMPLES OF MATERIAL | PUBLICATIONS |
|---|---|---|
| Triarylamine or polythiophene polymers with conductivity dopants | 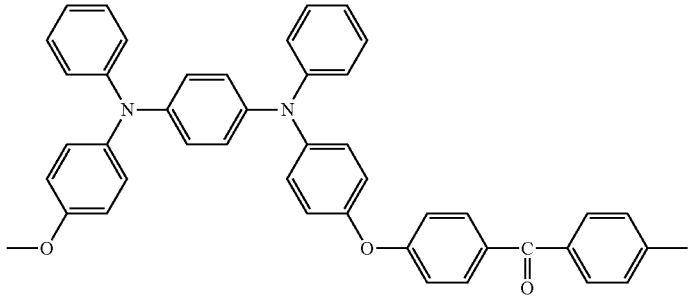 and 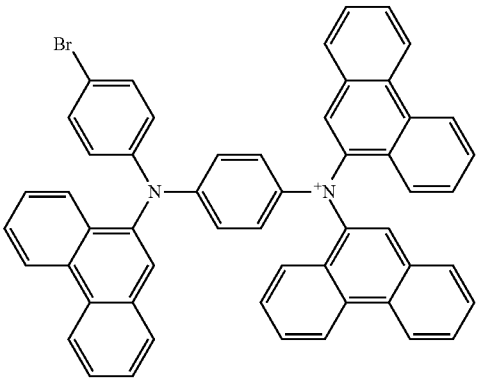 [SMILES: Brc1ccc(N(c2ccc([NH+](c3cc4ccccc4c4ccccc34)c3cc4ccccc4c4ccccc34)cc2)c2cc3ccccc3c3ccccc23)cc1] 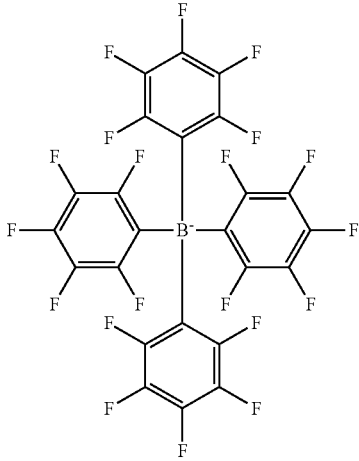 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | EP1725079A1 |
| Organic compounds with conductive inorganic compounds, such as molybdenum and tungsten oxides | 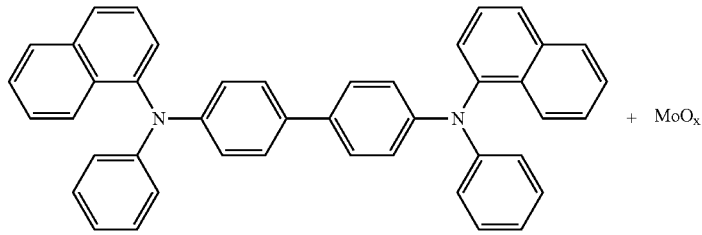 [SMILES: c1ccc(N(c2ccc(-c3ccc(N(c4ccccc4)c4cccc5ccccc45)cc3)cc2)c2cccc3ccccc23)cc1] + MoO$_x$ | US20050123751 SID Symposium Digest, 37, 923 (2006) WO2009018009 |

TABLE I-continued
| MATERIAL | EXAMPLES OF MATERIAL | PUBLICATIONS |
|---|---|---|
| n-type semiconducting organic complexes | 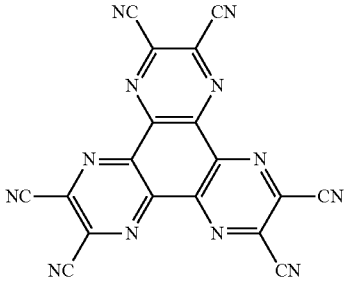 [SMILES: N#Cc1nc2c3nc(C#N)c(C#N)nc3c3nc(C#N)c(C#N)nc3c2nc1C#N] | US20020158242 |
| Metal organometallic complexes | 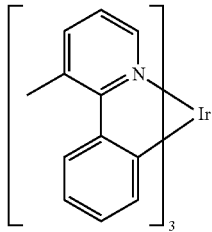 | US20060240279 |
| Cross-linkable compounds | 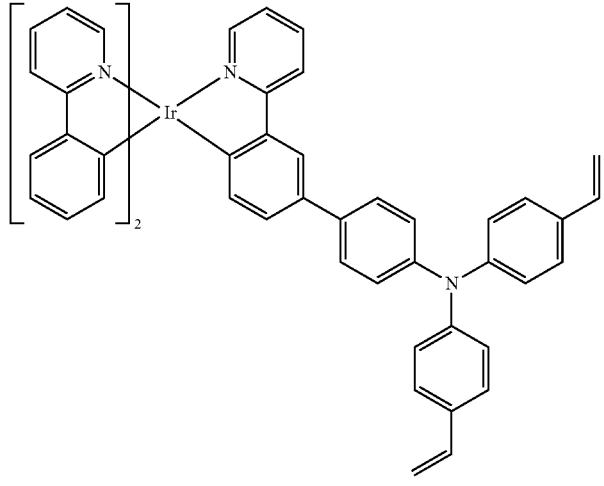 | US20080220265 |
| Polythiophene based polymers and copolymers | 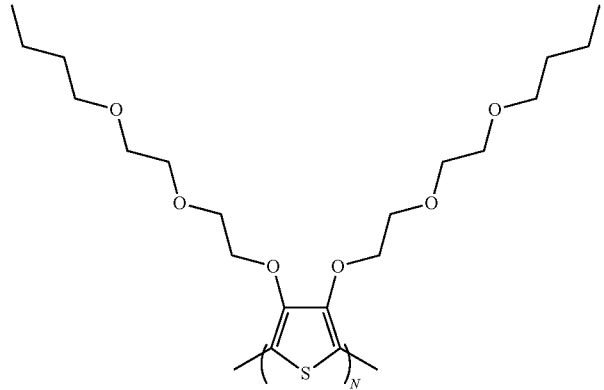 | WO 2011075644<br>EP2350216 |

TABLE I-continued

| MATERIAL | EXAMPLES OF MATERIAL | PUBLICATIONS |
|---|---|---|
| Hole transporting materials | | |
| Triarylamines (e.g., TPD, α-NPD) | | Appl. Phys. Lett. 51, 913 (1987) |
| | | U.S. Pat. No. 5,061,569 |
| | | EP650955 |

| MATERIAL | EXAMPLES OF MATERIAL | PUBLICATIONS |
|---|---|---|
| | 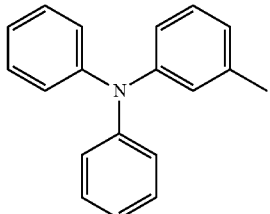 | J. Mater. Chem. 3, 319 (1993) |
| | 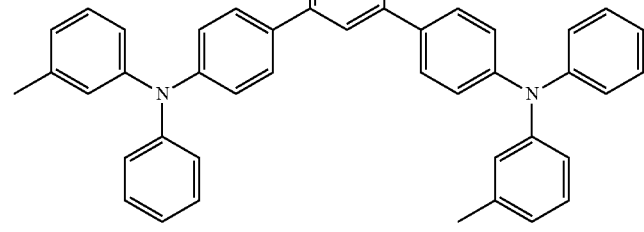 | Appl. Phys. Lett. 90, 183503 (2007) |
| | 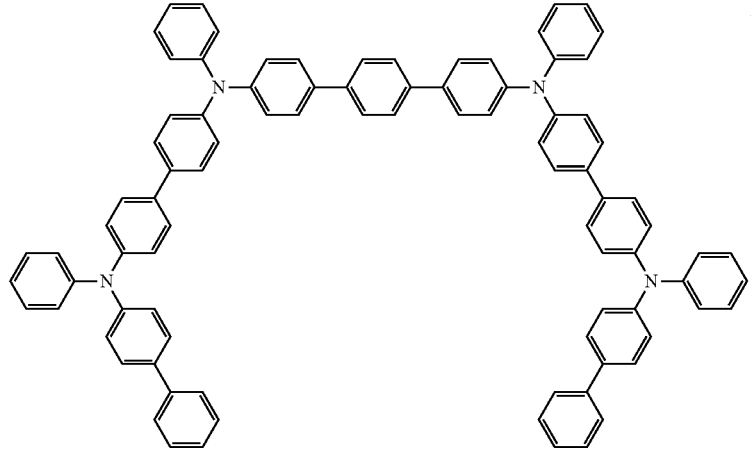 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE I-continued

| MATERIAL | EXAMPLES OF MATERIAL | PUBLICATIONS |
| --- | --- | --- |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |

TABLE I-continued
| MATERIAL | EXAMPLES OF MATERIAL | PUBLICATIONS |
| --- | --- | --- |
| Isoindole compounds | 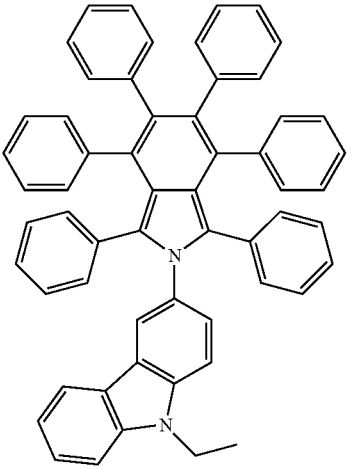 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 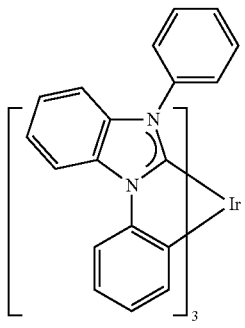 | US20080018221 |
Phosphorescent OLED host materials
Red hosts
| MATERIAL | EXAMPLES OF MATERIAL | PUBLICATIONS |
| --- | --- | --- |
| Arylcarbazoles | 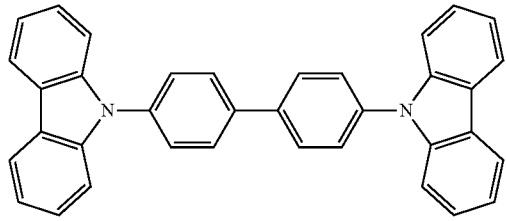 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., Alq$_3$, BALq) | 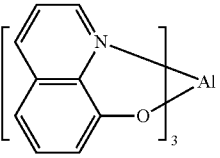 | Nature 395, 151 (1998) |
| | 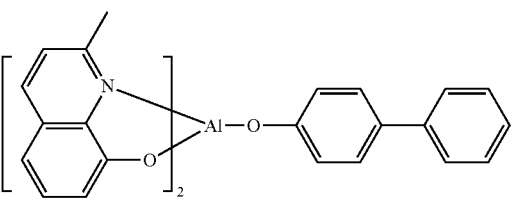 | US20060202194 |

TABLE I-continued

| MATERIAL | EXAMPLES OF MATERIAL | PUBLICATIONS |
| --- | --- | --- |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |

TABLE I-continued

| MATERIAL | EXAMPLES OF MATERIAL | PUBLICATIONS |
|---|---|---|
| Chrysene based compounds | | WO2011086863 |

Green hosts

| MATERIAL | EXAMPLES OF MATERIAL | PUBLICATIONS |
|---|---|---|
| Arylcarbazoles | | Appl. Phys. Lett. 78, 1622 (2001) |
| | | US20030175553 |
| | | WO2001039234 |
| Aryltriphenylene compounds | | US20060280965 |

| MATERIAL | EXAMPLES OF MATERIAL | PUBLICATIONS |
|---|---|---|
| | 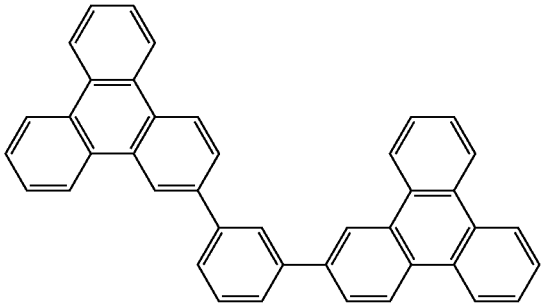 [SMILES: c1cc(-c2ccc3c4ccccc4c4ccccc4c3c2)cc(-c2ccc3c4ccccc4c4ccccc4c3c2)c1] | US20060280965 |
| | 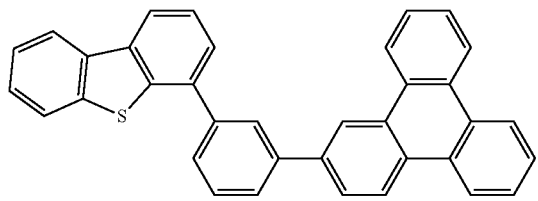 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 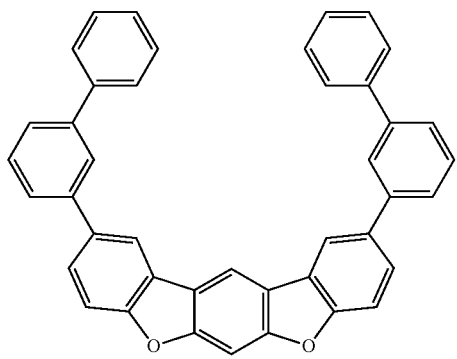 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 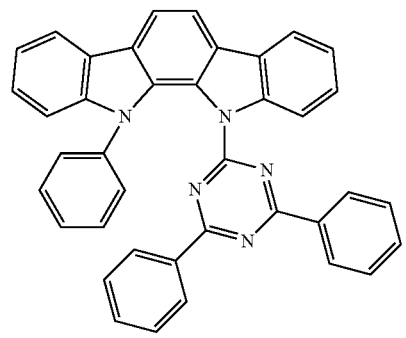 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 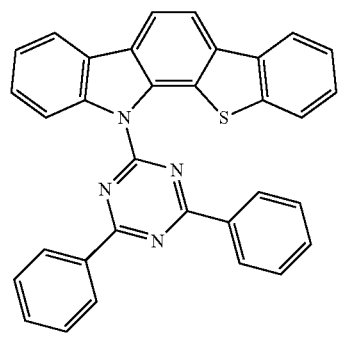 [SMILES: c1ccc(-c2nc(-c3ccccc3)nc(-n3c4ccccc4c4ccc5c6ccccc6sc5c43)n2)cc1] | WO2010107244 |

TABLE I-continued
| MATERIAL | EXAMPLES OF MATERIAL | PUBLICATIONS |
|---|---|---|
| Aza-carbazole/DBT/DBF | 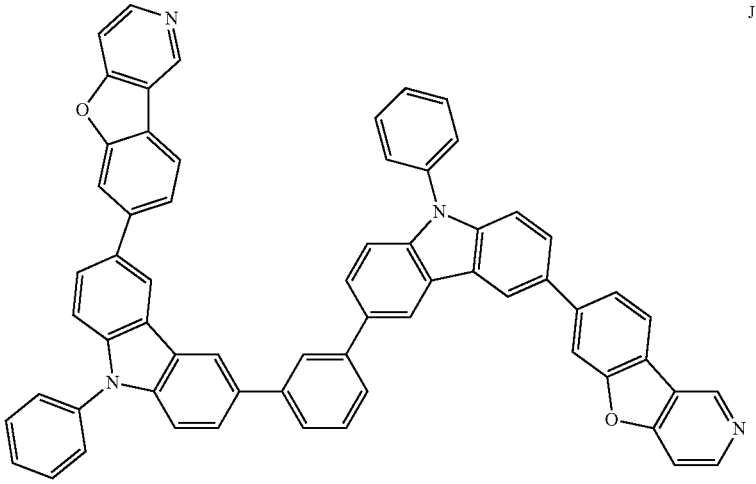 | JP2008074939 |
|  | 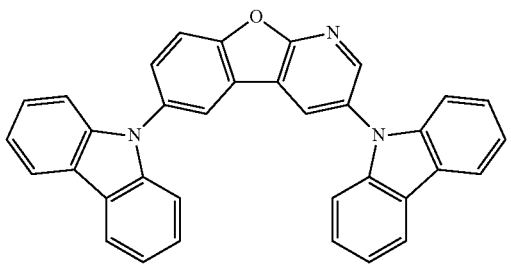 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 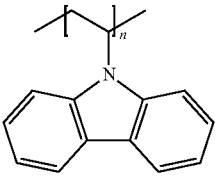 | Appl. Phys. Lett. 77, 2280 (2000) |
| Spirofluorene compounds | 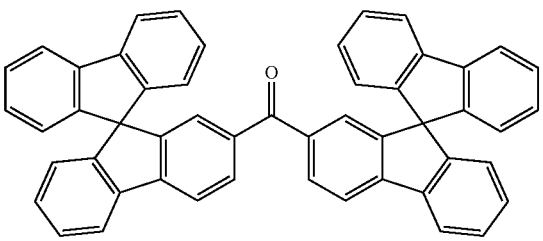 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 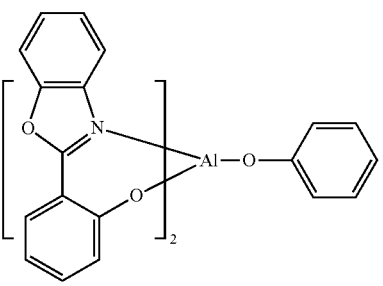 | WO2005089025 |

TABLE I-continued

| MATERIAL | EXAMPLES OF MATERIAL | PUBLICATIONS |
|---|---|---|
| | | WO2006132173 |
| | | JP200511610 |
| Spirofluorene-carbazole compounds | | JP2007254297 |
| | | JP2007254297 |
| Indolocabazoles | | WO2007063796 |

TABLE I-continued

| MATERIAL | EXAMPLES OF MATERIAL | PUBLICATIONS |
|---|---|---|
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |
| Metal phenoxypyridine compounds | | WO2005030900 |

TABLE I-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |

Blue hosts

| MATERIAL | EXAMPLES OF MATERIAL | PUBLICATIONS |
|---|---|---|
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

| MATERIAL | EXAMPLES OF MATERIAL | PUBLICATIONS |
|---|---|---|
| | 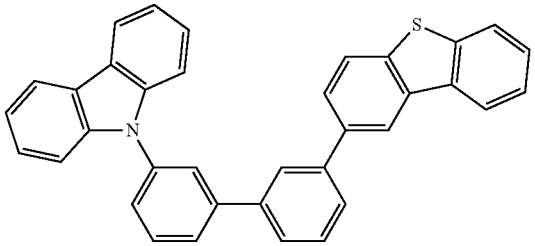 [SMILES: c1cc(-c2cccc(-n3c4ccccc4c4ccccc43)c2)cc(-c2ccc3sc4ccccc4c3c2)c1] | US20090030202<br>US20090017330 |
| | 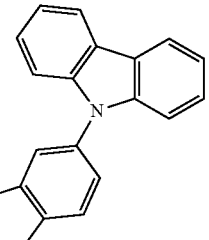 | US20100084966 |
| Silicon aryl compounds | 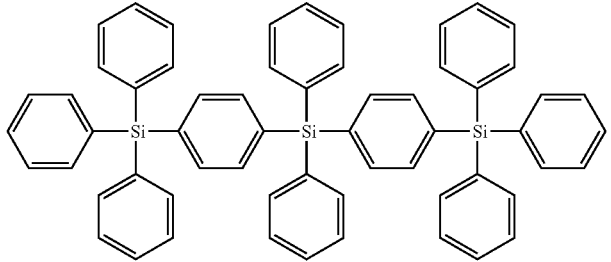 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 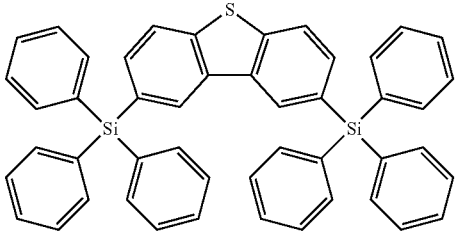 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 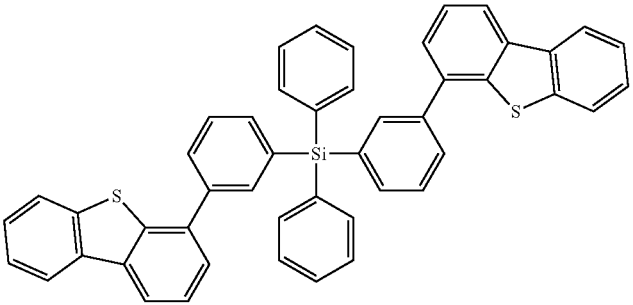 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 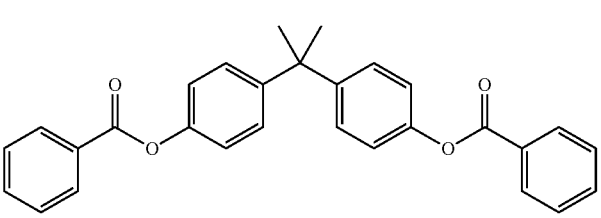 [SMILES: CC(C)(c1ccc(OC(=O)c2ccccc2)cc1)c1ccc(OC(=O)c2ccccc2)cc1] | WO2006100298 |

TABLE I-continued

| MATERIAL | EXAMPLES OF MATERIAL | PUBLICATIONS |
| --- | --- | --- |
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants

Red dopants

| Heavy metal porphyrins (e.g., PtOEP) | | Nature 395, 151 (1998) |
| --- | --- | --- |
| Iridium(III) organometallic complexes | | Appl. Phys. Lett. 78, 1622 (2001) |

TABLE I-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE I-continued

| MATERIAL | EXAMPLES OF MATERIAL | PUBLICATIONS |
|---|---|---|
| | (structure) | US20080261076<br>US20100090591 |
| | (structure) | US20070087321 |
| | (structure) | Adv. Mater. 19, 739 (2007) |
| | (structure) | WO2009100991 |
| | (structure) | WO2008101842 |

TABLE I-continued

| MATERIAL | EXAMPLES OF MATERIAL | PUBLICATIONS |
|---|---|---|
| | [Ir complex with two carbazolyl groups, Cl, and two PPh₃ ligands] | U.S. Pat. No. 7,232,618 |
| Platinum(II) organometallic complexes | [Pt complex with phenylisoquinoline and acetylacetonate ligands] | WO2003040257 |
| | [Pt complex with diarylamine and two pyridyl groups] | US20070103060 |
| Osminum(III) complexes | [Os(PPhMe₂)₂ complex with CF₃-pyrazolyl pyridine ligand, subscript 2] | Chem. Mater. 17, 3532 (2005) |
| Ruthenium(II) complexes | [Ru(PPhMe₂)₂ complex with tBu-pyrazolyl isoquinoline ligand, subscript 2] | Adv. Mater. 17, 1059 (2005) |
| Rhenium (I), (II), and (III) complexes | [Re(CO)₄ complex with 8-hydroxyquinoline ligand] | US20050244673 |

TABLE I-continued

| MATERIAL | EXAMPLES OF MATERIAL | PUBLICATIONS |
| --- | --- | --- |
| Green dopants | | |
| Iridium(III) organometallic complexes | and its derivatives | Inorg. Chem. 40, 1704 (2001) |
| | | US20020034656 |
| | | U.S. Pat. No. 7,332,232 |

TABLE I-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE I-continued
| MATERIAL | EXAMPLES OF MATERIAL | PUBLICATIONS |
|---|---|---|
| | 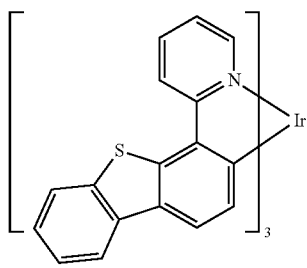 | U.S. Pat. No. 6,921,915 |
| | 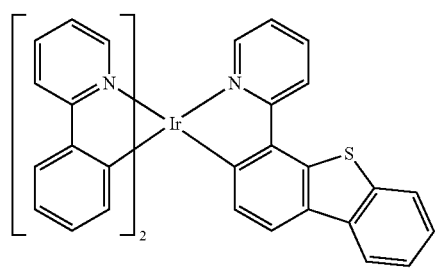 | US20100244004 |
| | 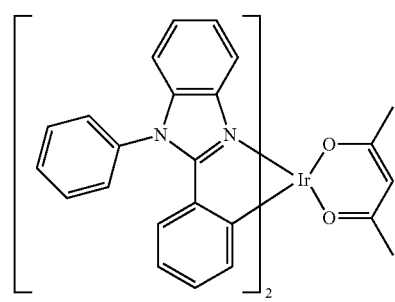 | U.S. Pat. No. 6,687,266 |
| | 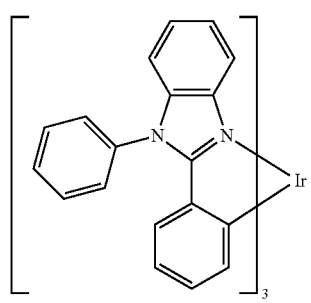 | Chem. Mater. 16, 2480 (2004) |
| | 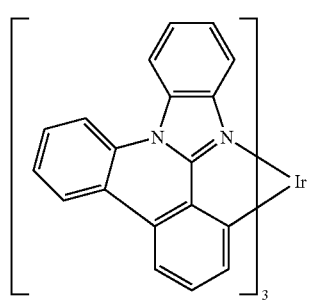 | US20070190359 |

TABLE I-continued

| MATERIAL | EXAMPLES OF MATERIAL | PUBLICATIONS |
|---|---|---|
| | | US 20060008670<br>JP2007123392 |
| | | WO2010086089,<br>WO2011044988 |
| | | Adv. Mater. 16, 2003<br>(2004) |
| | | Angew. Chem. Int. Ed.<br>2006, 45, 7800 |
| | | WO2009050290 |
| | | US20090165846 |

TABLE I-continued

| MATERIAL | EXAMPLES OF MATERIAL | PUBLICATIONS |
| --- | --- | --- |
| | | US20080015355 |
| | | US20010015432 |
| | | US20100295032 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |

TABLE I-continued
| MATERIAL | EXAMPLES OF MATERIAL | PUBLICATIONS |
|---|---|---|
| | 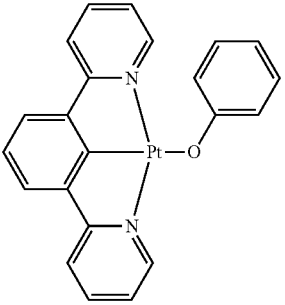 | Appl. Phys. Lett. 86, 153505 (2005) |
| | 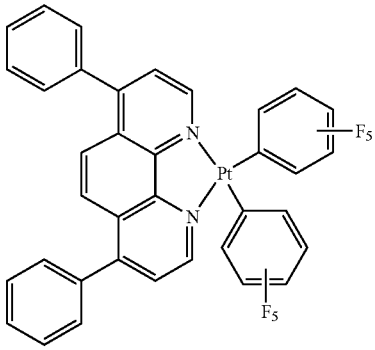 | Chem. Lett. 34, 592 (2005) |
| | 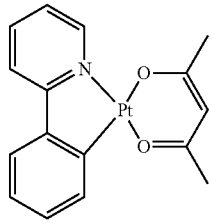 | WO2002015645 |
| | 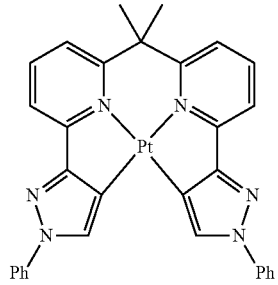 | US20060263635 |
| | 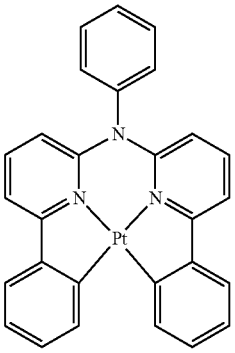 | US20060182992<br>US20070103060 |

| MATERIAL | EXAMPLES OF MATERIAL | PUBLICATIONS |
|---|---|---|
| Cu complexes | 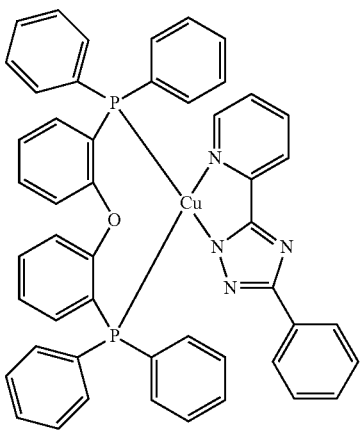 | WO2009000673 |
|  | 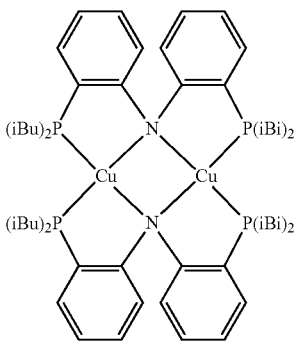 | US20070111026 |
| Gold complexes | 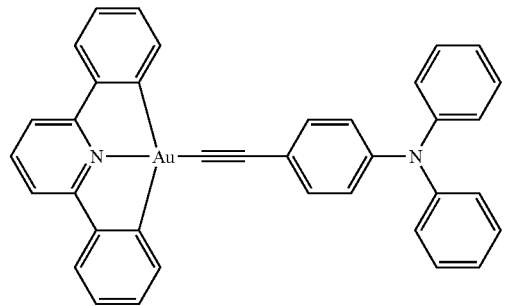 | Chem. Commun. 2906 (2005) |
| Rhenium(III) complexes |  | Inorg. Chem. 42, 1248 (2003) |

TABLE I-continued

| MATERIAL | EXAMPLES OF MATERIAL | PUBLICATIONS |
| --- | --- | --- |
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE I-continued

| MATERIAL | EXAMPLES OF MATERIAL | PUBLICATIONS |
|---|---|---|
| Blue dopants | | |
| Iridium(III) organometallic complexes | | WO2002002714 |
| | | WO2006009024 |
| | | US20060251923<br>US20110057559<br>US20110204333 |
| | | U.S. Pat. No. 7,393,599,<br>WO2006056418,<br>US20050260441,<br>WO2005019373 |
| | | U.S. Pat. No. 7,534,505 |
| | | WO2011051404 |

TABLE I-continued

| MATERIAL | EXAMPLES OF MATERIAL | PUBLICATIONS |
|---|---|---|
| | | U.S. Pat. No. 7,445,855 |
| | | US20070190359, US20080297033 US20100148663 |
| | | U.S. Pat. No. 7,338,722 |
| | | US20020134984 |
| | | Angew. Chem. Int. Ed. 47, 1 (2008) |

TABLE I-continued
| MATERIAL | EXAMPLES OF MATERIAL | PUBLICATIONS |
|---|---|---|
| | 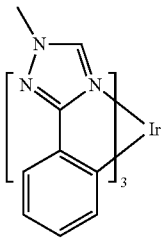 | Chem. Mater. 18, 5119 (2006) |
| | 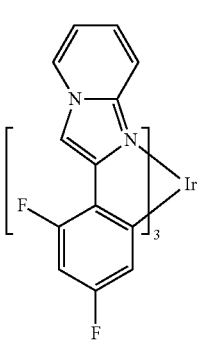 | Inorg. Chem. 46, 4308 (2007) |
| | 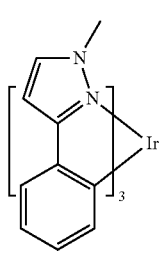 | WO2005123873 |
| | 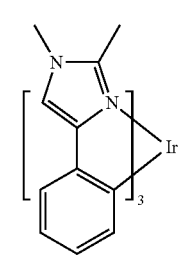 | WO2005123873 |
| | 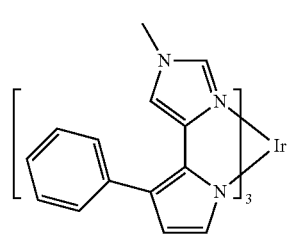 | WO2007004380 |

| MATERIAL | EXAMPLES OF MATERIAL | PUBLICATIONS |
|---|---|---|
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE I-continued

| MATERIAL | EXAMPLES OF MATERIAL | PUBLICATIONS |
| --- | --- | --- |
| Pt tetradentate complexes with at least one metal-carbene bond | 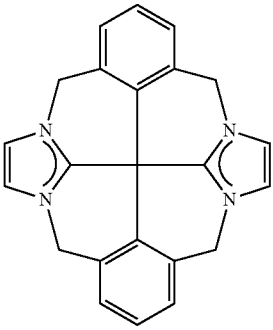 [SMILES: C1=CN2Cc3cccc4c3C35c6c(cccc6CN6C=CN(C4)C63)CN1C25] | U.S. Pat. No. 7,655,323 |

Exciton/hole blocking layer materials

| MATERIAL | EXAMPLES OF MATERIAL | PUBLICATIONS |
| --- | --- | --- |
| Bathocuprine compounds (e.g., BCP, BPhen) | 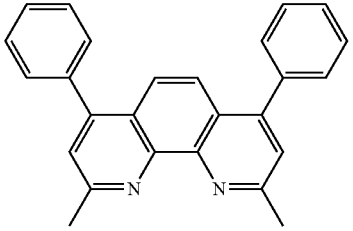 [SMILES: Cc1cc(-c2ccccc2)c2ccc3c(-c4ccccc4)cc(C)nc3c2n1] | Appl. Phys. Lett. 75, 4 (1999) |
| | 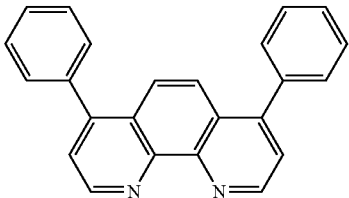 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 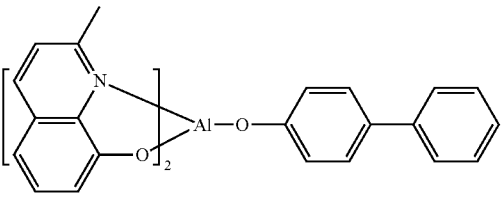 | Appl. Phys. Lett. 81, 162 (2002) |
| 5-member ring electron deficient heterocycles such as triazole, oxadiazole, imidazole, benzoimidazole | 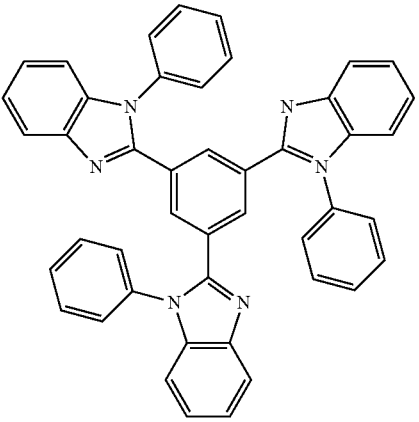 | Appl. Phys. Lett. 81, 162 (2002) |

TABLE I-continued
| MATERIAL | EXAMPLES OF MATERIAL | PUBLICATIONS |
|---|---|---|
| Triphenylene compounds | 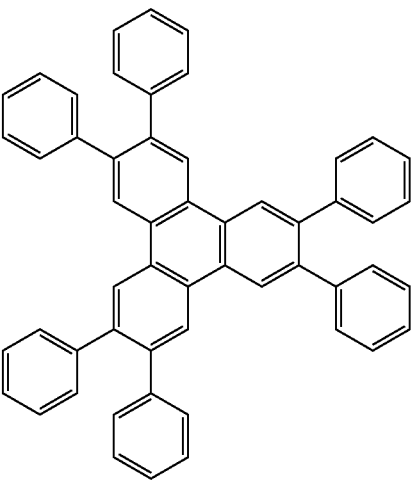 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 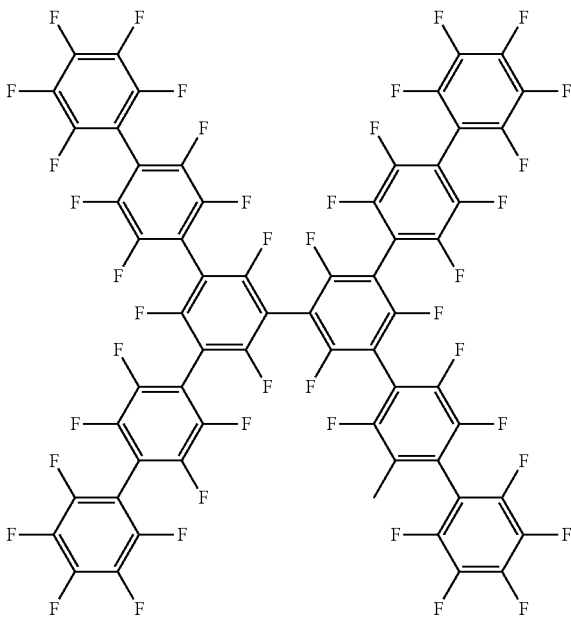 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 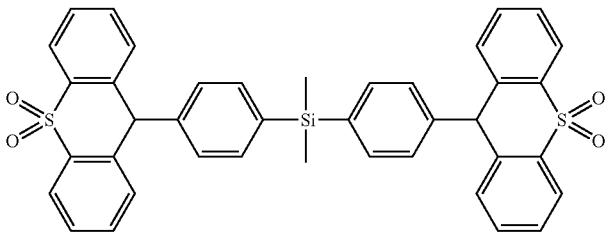 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 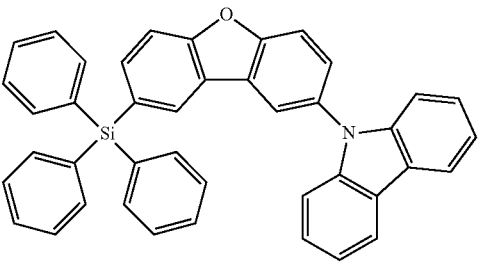 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE I-continued
| MATERIAL | EXAMPLES OF MATERIAL | PUBLICATIONS |
|---|---|---|
| Aza-carbazoles | 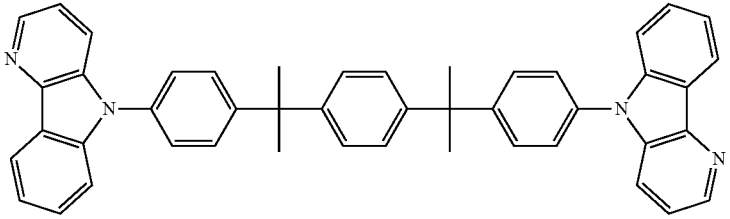 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 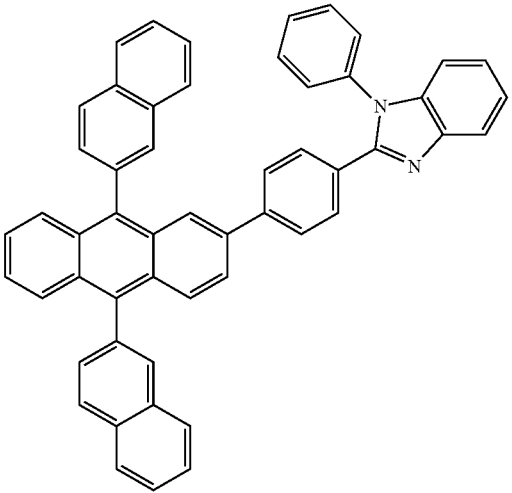 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 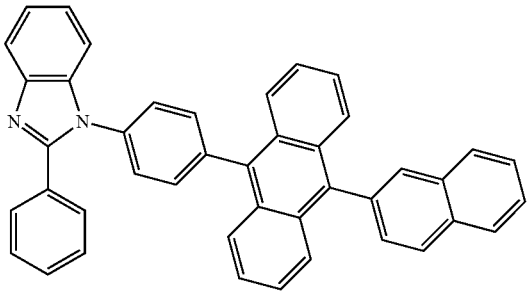 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 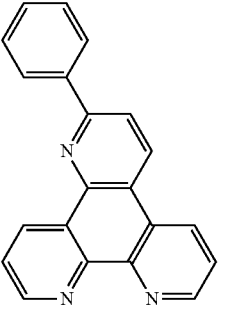 [SMILES: c1ccc(-c2ccc3c4cccnc4c4ncccc4c3n2)cc1] | US20090115316 |
| Anthracene-benzothiazole compounds | 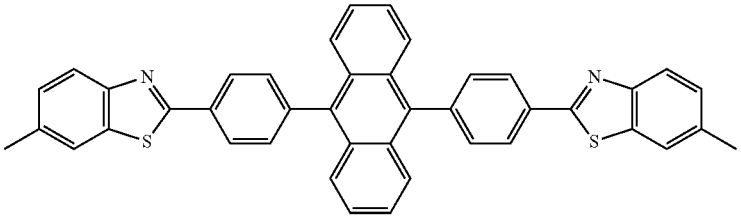 | Appl. Phys. Lett. 89, 063504 (2006) |

TABLE I-continued

| MATERIAL | EXAMPLES OF MATERIAL | PUBLICATIONS |
| --- | --- | --- |
| Metal 8-hydroxyquinolates (e.g., Alq$_3$, Zrq$_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE I-continued

| MATERIAL | EXAMPLES OF MATERIAL | PUBLICATIONS |
|---|---|---|
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |
| Triazine complexes | | US20040036077 |

| MATERIAL | EXAMPLES OF MATERIAL | PUBLICATIONS |
|---|---|---|
| Zn (N^N) complexes | 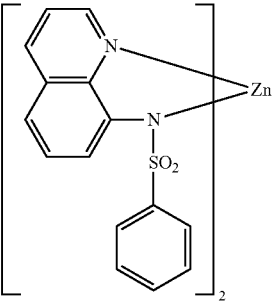 | U.S. Pat. No. 6,528,187 |

Computational Examples

Calculation of Singlet and Triplet Transitions

Synthesis of Compound 5-O-1

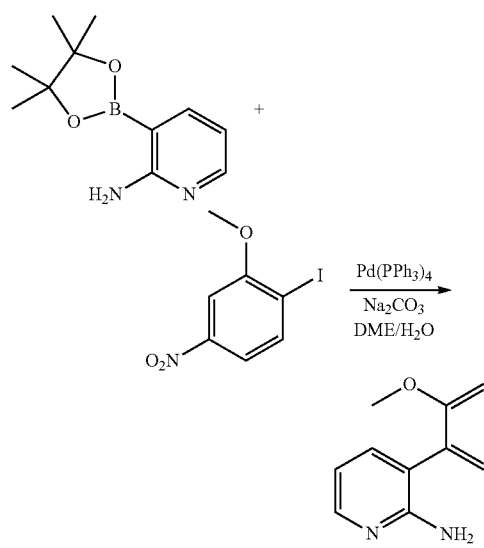

Synthesis of 3-(2-methoxy-4-nitrophenyl)pyridin-2-amine 3-(4,4,5,5-tetramethyl-1,3,2-dioxaborolan-2-yl)pyridin-2-amine (20 g, 91 mmol), 1-iodo-2-methoxy-4-nitrobenzene (23 g, 83 mmol), Pd(PPh$_3$)$_4$ (1 g, 0.83 mmol) and sodium carbonate (26 g, 248 mmol) were added to DME (300 mL) and water (200 mL) and the reaction mixture degassed thoroughly before being heated to reflux for 16 h. The reaction was cooled to room temperature and partitioned between EtOAc and water. The layers were separated and the aqueous extracted twice with EtOAc. The combined organic layers were dried over sodium sulfate, filtered and rotovapped. The crude material was lixiviated with EtOAc to give 5.0 g of product. The filtrate was chromatographed on silica gel with 1/1 hexane/EtOAc to EtOAc to give another 4.4 g of product. The total yield of 3-(2-methoxy-4-nitrophenyl)pyridin-2-amine was 9.4 g (46%). The product was confirmed by NMR.

Synthesis of 7-nitrobenzofuro[2,3-b]pyridine 3-(2-methoxy-4-nitrophenyl)pyridin-2-amine (9.4 g, 38.3 mmol) was dissolved in acetic acid (60 mL) and THF (20 mL) and the reaction mixture cooled to −10° C. in a salt/ice/water bath. t-Butyl nitrite (9.1 mL, 77.0 mmol) was added dropwise, which caused the reaction to become thick. The reaction mixture was allowed to slowly warm to room temperature overnight and partitioned between EtOAc and water. The aqueous was washed twice with EtOAc and the combined organics twice with water. The organics were dried over sodium sulfate and stripped to give 9.2 g of a yellow solid. The crude material was chromatographed on silica gel with 99/1 to 95/5 DCM/EtOAc to give 5.0 g (61%) of 7-nitrobenzofuro[2,3-b]pyridine as an off-white solid. The product was confirmed by NMR.

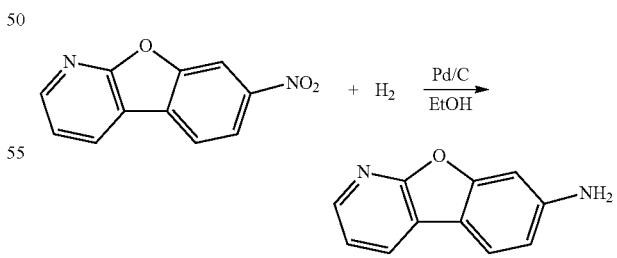

Synthesis of benzofuro[2,3-b]pyridin-7-amine

Palladium on carbon (1.2 g) was added to 7-nitrobenzofuro[2,3-b]pyridine (5 g, 23.4 mmol) in 200 mL of ethanol and reduced with hydrogen on Parr hydrogenator for 2 h. GC/MS indicated reaction completion and the contents were filtered through a plug of Celite® and washed with DCM. After evaporation of the solvent, the crude product was chromatographed on silica 0-10% ethyl acetate in DCM to yield 3.9 g (91%) benzofuro[2,3-b]pyridin-7-amine. The product was confirmed by NMR.

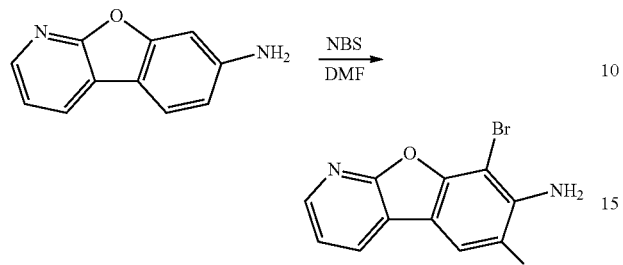

Synthesis of 6,8-dibromobenzofuro[2,3-b]pyridin-7-amine

Benzofuro[2,3-b]pyridin-7-amine (6.6 g, 35.8 mmol) was suspended in DMF (35 mL) and cooled to 0° C. N-bromosuccinimide (12.8 g, 71.7 mmol) was dissolved in DMF (35 mL) and added dropwise to the amine mixture and the reaction solution was allowed to warm slowly to room temperature overnight. The reaction mixture was poured into 250 mL of aq. NaHCO$_3$, stirred for 10 min. and the contents filtered, washing with copious water. The filtered solid was triturated with hexane/EtOAc and dried to give 12 g (98%) of 6,8-dibromobenzofuro[2,3-b]pyridin-7-amine as a tan solid. The product was confirmed by NMR.

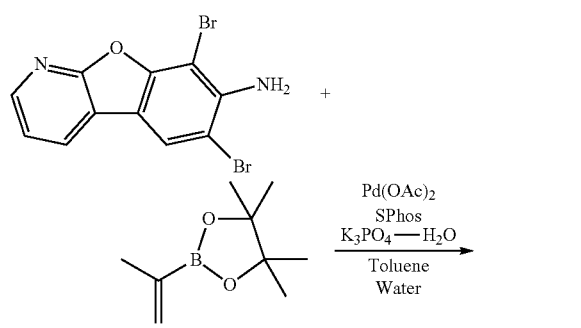

Synthesis of 6,8-di(prop-1-en-2-yl)benzofuro[2,3-b]pyridin-7-amine 6,8-Dibromobenzofuro[2,3-b]pyridin-7-amine (11 g, 32.2 mmol), 4,4,5,5-tetramethyl-2-(prop-1-en-2-yl)-1,3,2-dioxaborolane (25.3 mL, 149 mmol), palladium(II) acetate (1.1 g, 4.8 mmol), dicyclohexyl(2',6'-dimethoxy-[1,1'-biphenyl]-3-yl)phosphine (4.0 g, 9.7 mmol) and potassium phosphate tribasic monohydrate (37.0 g, 161 mmol) were added to toluene (120 mL) and water (120 mL) and the mixture degassed thoroughly before being heated to reflux overnight. After cooling, the reaction mixture was partitioned between EtOAc and water. The aqueous was washed twice with EtOAc and the combined organics twice with water. The organics were dried over sodium sulfate and stripped and the crude material was chromatographed on silica gel to give 7.1 g (84%) of 6,8-di(prop-1-en-2-yl)benzofuro[2,3-b]pyridin-7-amine. The product was confirmed by GC/MS and NMR.

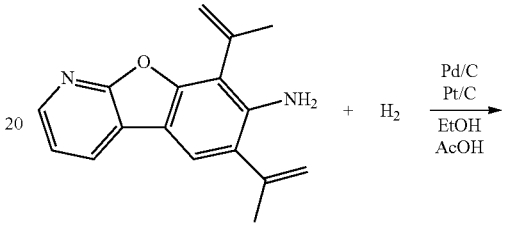

Synthesis of 6,8-diisopropylbenzofuro[2,3-b]pyridin-7-amine

Palladium on carbon (1.4 g) and platinum on carbon (2.6 g) were added to 6,8-di(prop-1-en-2-yl)benzofuro[2,3-b]pyridin-7-amine (7.1 g, 26.9 mmol) in 150 mL of ethanol and 2 mL acetic acid and reduced with hydrogen on Parr hydrogenator for 16 h. GC/MS indicated reaction completion and the contents were filtered through a plug of Celite® and washed with DCM. After evaporation of the solvent, the crude product was chromatographed on silica with 80:10:10 hexane:EtOAc:DCM to give 4.8 g (67%) of 6,8-diisopropylbenzofuro[2,3-b]pyridin-7-amine. The product was confirmed by GC/MS and NMR.

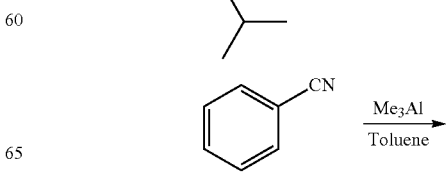

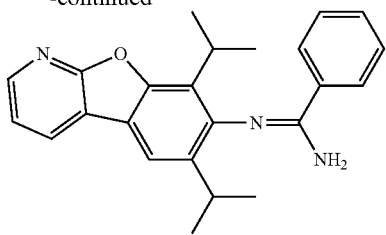

Synthesis of N'-(6,8-diisopropylbenzofuro[2,3-b]pyridin-7-yl)benzimidamide 6,8-Diisopropylbenzofuro[2,3-b]pyridin-7-amine (4.7 g, 17.5 mmol) was dissolved in toluene (100 mL) and cooled to 0° C. Trimethylaluminum (17.5 mL, 35.0 mmol) (2.0 M in toluene) was added dropwise and the reaction mixture was warmed to room temperature and stirred for 2 h. Benzonitrile (2.3 mL, 22.8 mmol) in toluene (60 mL) was then added dropwise and the reaction heated to 90° C. overnight. The reaction was cooled and poured portionwise into a beaker containing 100 g of silica, 200 mL of DCM and 100 mL of MeOH causing some gas evolution and minor exotherm. The mixture was stirred for one hour, filtered over Celite® and washed with ~9:1 DCM:MeOH until the eluent showed no luminescence on TLC (~1 L total volume). The eluent was stripped to give 7.2 g of a yellow solid that was lixiviated with hexane to give 6.3 g (97%) of N'-(6,8-diisopropylbenzofuro[2,3-b]pyridin-7-yl)benzimidamide as an off-white solid. The product was confirmed by GC/MS and NMR.

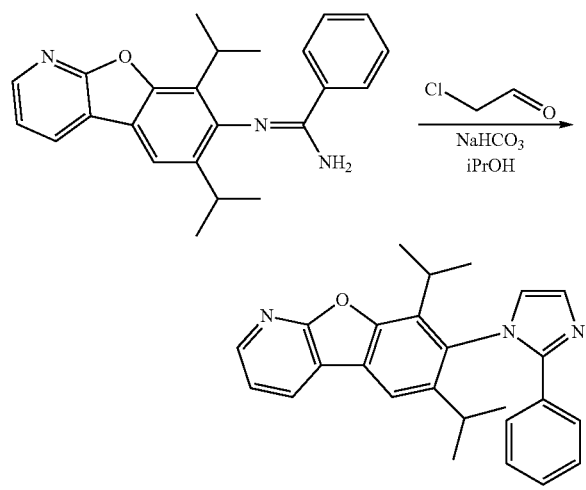

Synthesis of 6,8-diisopropyl-7-(2-phenyl-1H-imidazol-1-yl)benzofuro[2,3-b]pyridine N'-(6,8-Diisopropylbenzofuro[2,3-b]pyridin-7-yl)benzimidamide (6.3 g, 16.9 mmol) was added to 2-propanol (200 mL) and 2-chloroacetaldehyde (5.3 g, 33.9 mmol) (50% in water) and sodium bicarbonate (4.3 g, 50.9 mmol) were added. The reaction mixture was heated to reflux overnight, cooled to room temperature and partitioned between EtOAc and water. After separation, the aqueous was washed twice with EtAOc and the combined organics twice with 10% LiCl (aq.). The combined organics were dried and rotovapped and the crude material was dissolved in 100 mL of toluene and 25 mL of acetic anhydride was added. The solution was heated to reflux overnight, cooled to RT and quenched with MeOH. All solvents were removed under reduced pressure and the resulting residue was chromatographed on silica gel with 9/1 hexane/EtOAc to 9/1 hexane/EtOAc gradient to give 5.7 g (85%) of 6,8-diisopropyl-7-(2-phenyl-1H-imidazol-1-yl)benzofuro[2,3-b]pyridine. The product was confirmed by GC/MS and NMR.

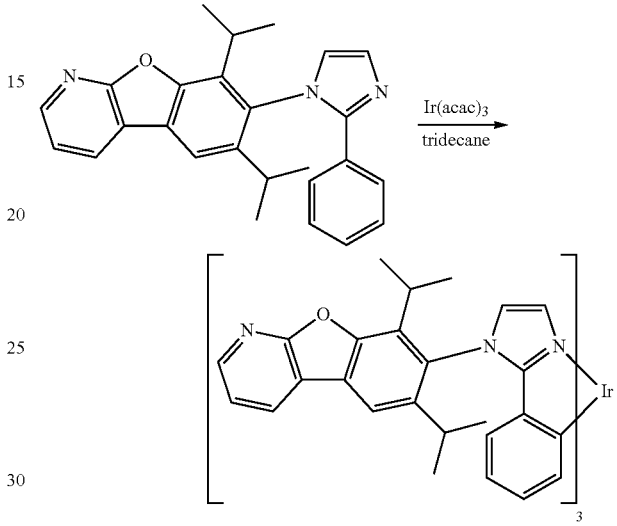

Synthesis of Compound 5-O-1

6,8-Diisopropyl-7-(2-phenyl-1H-imidazol-1-yl)benzofuro[2,3-b]pyridine (4.0 g, 10.1 mmol), Ir(acac)$_3$ (0.99 g, 2.0 mmol) and 20 drops of tridecane were added to a Schlenk flask and degassed thoroughly. The reaction was heated to 255° C. (bath temp.) for 60 h in a sand bath before cooling to room temperature. The reaction mixture was taken up in DCM and chromatographed on silica gel with a gradient from DCM to 95/5 DCM/EtOAc. This material was dissolved in DCM and precipitated with iPrOH to give 1.2 g (43%) of BD649. The product was confirmed by LC/MS and NMR.

TABLE III

Properties of Compound 5-O-1 and Compound A

| Compound | Redox Properties (vs Fc/Fc$^+$) | $\lambda_{max}$ of PL in 2-MeTHF |
|---|---|---|
| Compound 5-O-1 | $E_{red}$: −2.62 V; $R_{ox}$: 0.04 V | 476 nm |
| Compound A | $E_{red}$: −2.89 V; $R_{ox}$: 0.05 V | 474 nm |

Table III shows the oxidation and reduction potentials (measured in dry DMF with 0.1M NBu$_4$PF$_6$ as electrolyte) and photoluminescence emission wavelengths of Compound 5-O-1 and Compound A at room temperature. It has been unexpectedly discovered that compared to Compound A, the inventive compound is much easier to reduce but able to keep nearly the same color (only 2 nm difference in $\lambda_{max}$). The reduction potential of Compound 5-O-1 is 0.27 V lower than Compound A, which is highly desired in order to achieve a much more stable device while maintaining the same blue color emission.

DFT calculations with the Gaussian software package at the B3LYP/cep-31g functional and basis set were carried out for the compounds shown below in TABLE II. TABLE II shows the calculated values for the HOMO and the LUMO, and shows the respective HOMO-LUMO gap, as well as the wavelengths of light corresponding to the singlet $S_1$ and triplet $T_1$ transitions. The HOMO levels of the azadibenzofuran and azadibenzothiphene C-ring complexes shifted very slightly away from the vacuum level compared to the dibenzofuran and dibenzothiophene C-ring complexes. However, the LUMO levels shifted away from the vacuum level significantly as much as 0.44 eV. It is believed that a stabilized LUMO increases the stability of the compound to electrons, resulting in complexes with better stability in devices. Therefore, the inventive complexes with azadibenzofuran and azadibenzothiophene C-ring may provide better stability than the comparative compounds. In addition, although the calculated singlet energy of the inventive compounds red shifted significantly compared to comparative compounds, the triplet energy shift was negligible. The inventive compounds maintain blue emission.

TABLE II

| Compounds | HOMO | LUMO | Gap (eV) | $S_1$ (nm) | $T_1$ (nm) |
|---|---|---|---|---|---|
| Compound 1-O-1 | −4.96 | −1.79 | 3.17 | 445 | 466 |
| Compound 2-O-1 | −4.92 | −1.82 | 3.1 | 450 | 464 |
| Compound 3-O-1 | −4.95 | −1.67 | 3.27 | 427 | 464 |
| Compound 4-O-1 | −4.95 | −1.87 | 3.09 | 453 | 465 |

TABLE II-continued

| Compounds | HOMO | LUMO | Gap (eV) | S₁ (nm) | T₁ (nm) |
|---|---|---|---|---|---|
| Compound 5-O-1 | −4.92 | −1.81 | 3.12 | 447 | 464 |
| Compound A (Comparative Compound) | −4.89 | −1.42 | 3.47 | 400 | 464 |
| Compound 1-S-1 | −4.97 | −1.77 | 3.2 | 441 | 467 |
| Compound 2-S-1 | −4.92 | −1.79 | 3.13 | 445 | 464 |
| Compound 3-S-1 | −4.95 | −1.68 | 3.27 | 438 | 465 |

| Compounds | HOMO | LUMO | Gap (eV) | S₁ (nm) | T₁ (nm) |
|---|---|---|---|---|---|
| 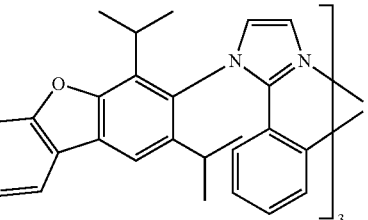 Compound 4-S-1 | −4.97 | −1.88 | 3.08 | 454 | 465 |
| 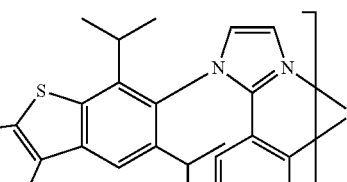 Compound 5-S-1 | −4.94 | −1.79 | 3.15 | 443 | 465 |
| 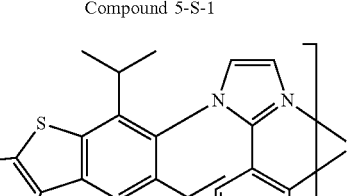 Compound B (Comparative Compound) | −4.91 | −1.44 | 3.46 | 401 | 464 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A compound having a structure of Formula (III):

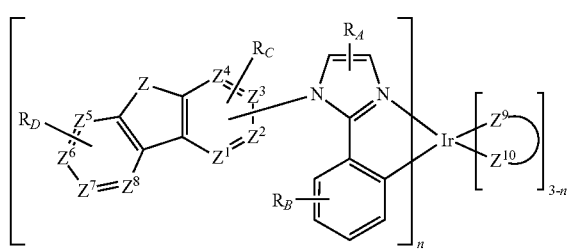

(III)

wherein $Z^9$-$Z^{19}$ is a bidentate ligand;
wherein n is 1, 2, or 3;
wherein $R_B$ and $R_D$ each represent mono, di, tri, tetra substitutions, or no substitution;
wherein $R_A$ represents mono, di, or no substitution;
wherein $R_C$ represents mono, di, tri, or no substitution;
wherein $Z^1$, $Z^2$, $Z^3$, $Z^4$, $Z^5$, $Z^6$, $Z^7$, and $Z^8$ are each selected from N or C;
wherein at least one of $Z^1$, $Z^2$, $Z^3$, $Z^4$, $Z^5$, $Z^6$, $Z^7$, and $Z^8$ is N;
wherein one of $Z^1$, $Z^2$, $Z^3$, and $Z^4$ is C that is bonded to N of A;
wherein Z is selected from the group consisting of BR, PR, O, S, Se, C=O, S=O, SO₂, CRR', SiRR', and GeRR';
wherein R, R', $R_A$, $R_B$, $R_C$, and $R_D$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein any two adjacent R, $R_A$, $R_C$, and $R_D$ are optionally joined to form a ring, which may be further substituted;
wherein the ligands may be linked with other ligands to form a tetradentate or hexadentate ligand;

wherein:
if $Z^1$ is bonded to N of ring A, then $Z^2$ is CR";
if $Z^2$ is bonded to N of ring A, then both $Z^1$ and $Z^3$ are CR";
if $Z^3$ is bonded to N of ring A, then both $Z^2$ and $Z^4$ are CR"; or
if $Z^4$ is bonded to N of ring A, then $Z^3$ is CR"; and
wherein R" is alkyl, cycloalkyl, aryl, or substituted aryl.

2. The compound of claim 1, wherein the compound is homoleptic.

3. The compound of claim 1, wherein the compound is heteroleptic.

4. The compound of claim 1, wherein only one of $Z^1$, $Z^2$, $Z^3$, $Z^4$, $Z^5$, $Z^6$, $Z^7$, and $Z^8$ is N.

5. The compound of claim 1, wherein Z is O or S.

6. The compound of claim 1, wherein R" is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, and combinations thereof.

7. The compound of claim 1, wherein $Z^9Z^{10}$ is selected from the group consisting of 1-phenylimidazole, 2-phenylpyridyl, 1-(4-dibenzofuran)imidazole, and 1-(4-dibenzothiophene)imidazole, each of which is optionally substituted one or more times by substituents selected independently from the group consisting of alkyl, cycloalkyl, aryl, heteroaryl, and combinations thereof.

8. The compound of claim 1 selected from the group consisting of:

Compound 1-X

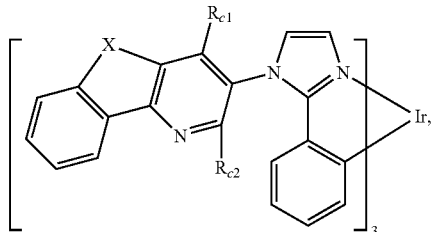

Compound 2-X

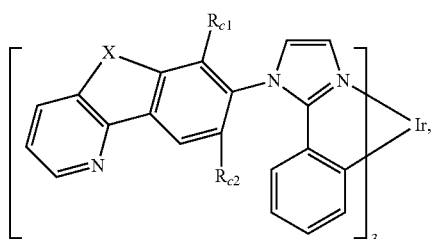

Compound 3-X

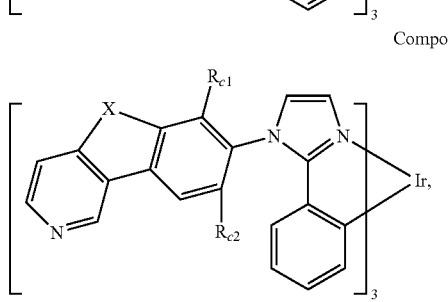

Compound 4-X

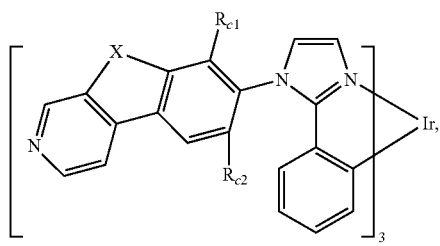

Compound 5-X

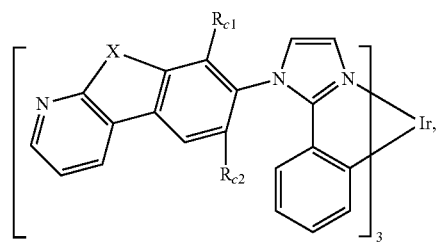

Compound 6-X

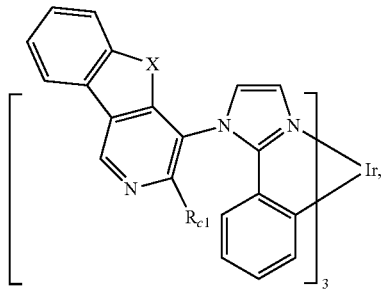

Compound 7-X

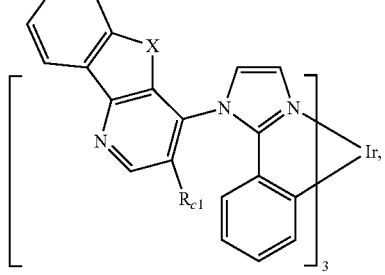

Compound 8-X

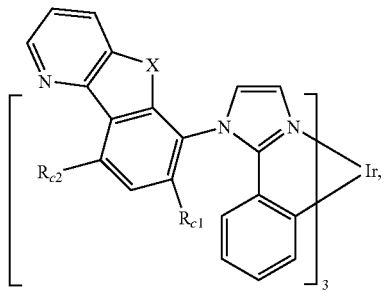

-continued
Compound 9-X
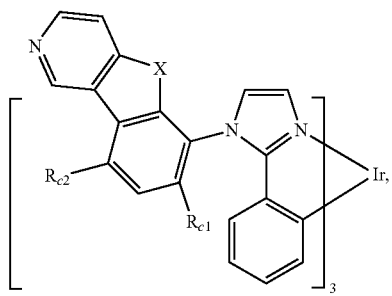
Compound 10-X
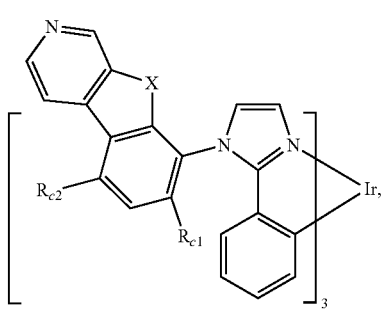
Compound 11-X
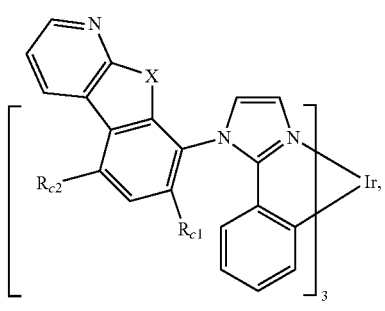
Compound 12-X
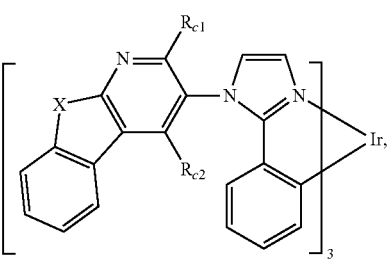
Compound 13-X
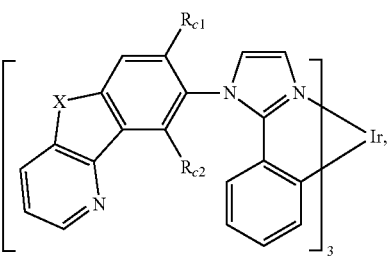
-continued
Compound 14-X
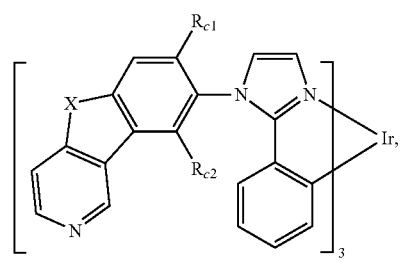
Compound 15-X
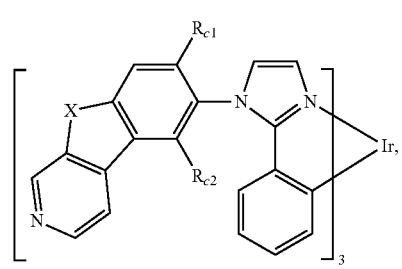
Compound 16-X
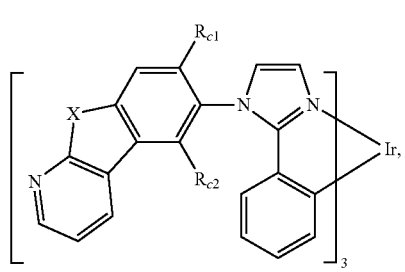
Compound 17-X
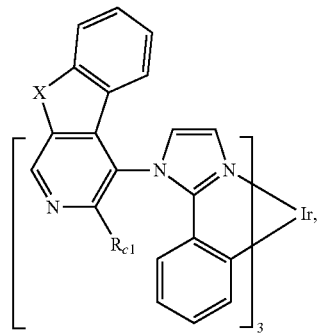
Compound 18-X
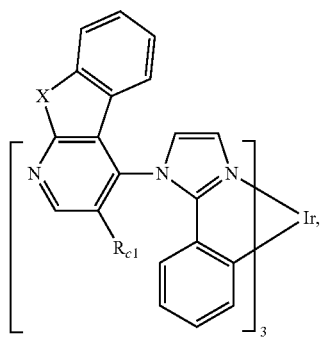

Compound 19-X
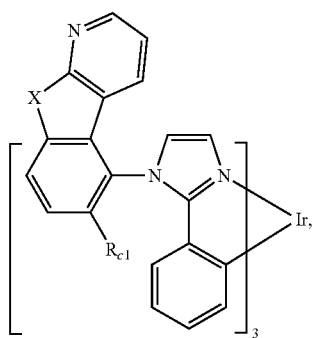
Compound 20-X
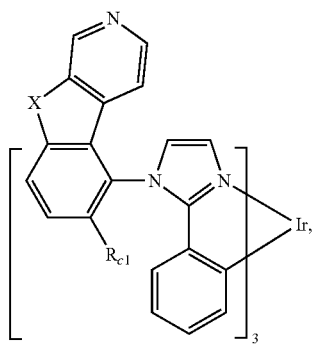
Compound 21-X
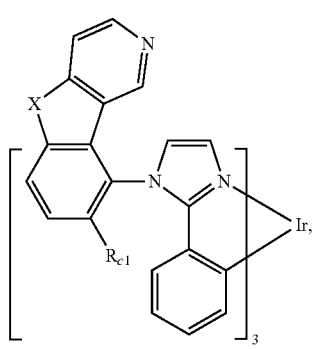
Compound 22-X
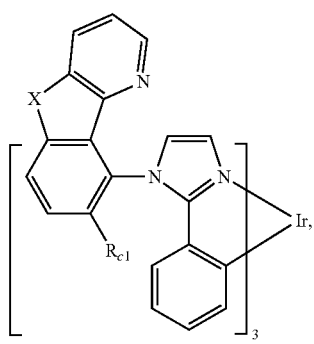
Compound 23-X
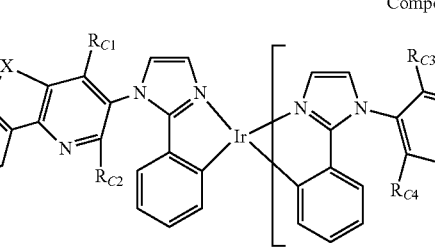
Compound 24-X
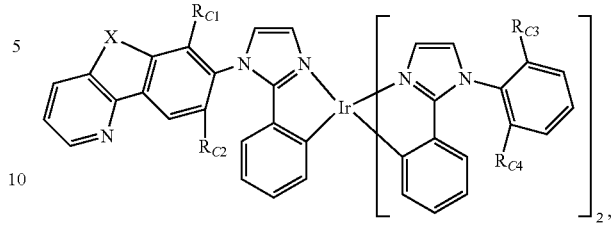
Compound 25-X
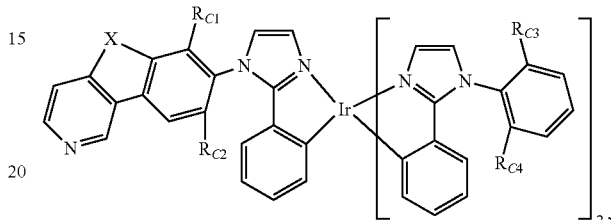
Compound 26-X
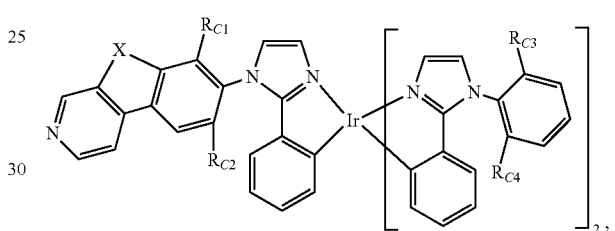
Compound 27-X
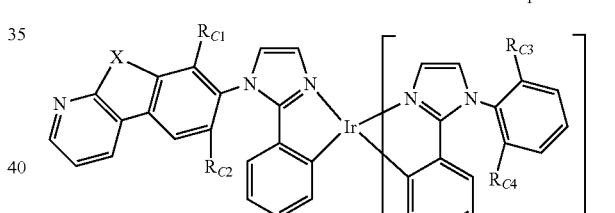
Compound 28-X
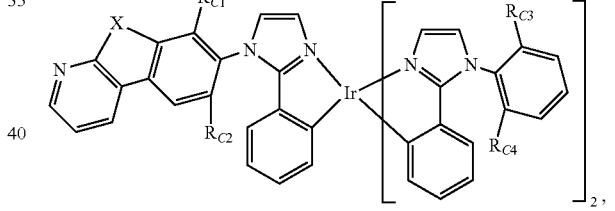
Compound 29-X
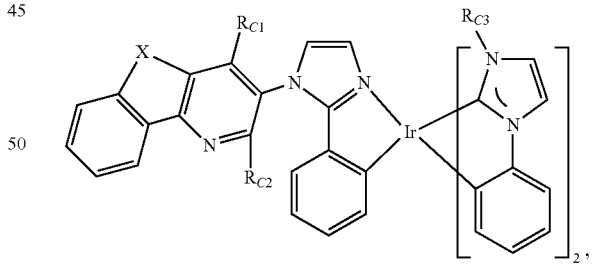

-continued
Compound 30-X
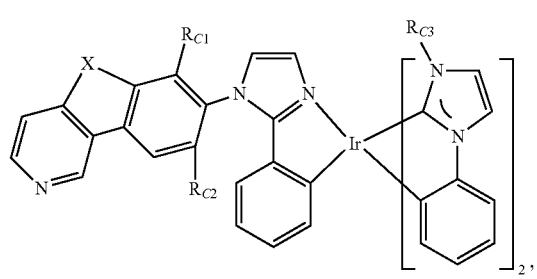
Compound 31-X
Compound 32-X
Compound 33-X
Compound 34-X
-continued
Compound 35-X
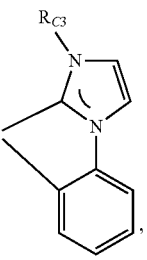
Compound 36-X
Compound 37-X
Compound 38-X
Compound 39-X Compound 40-X

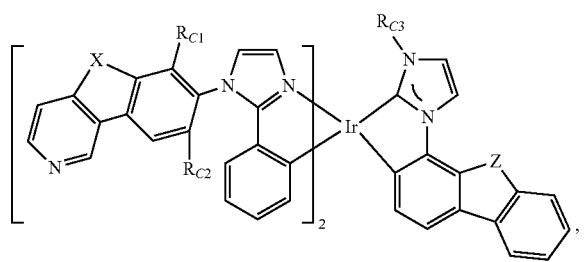

Compound 41-X

Compound 42-X

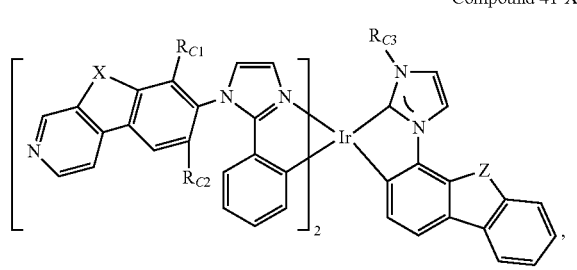

Compound 43-X

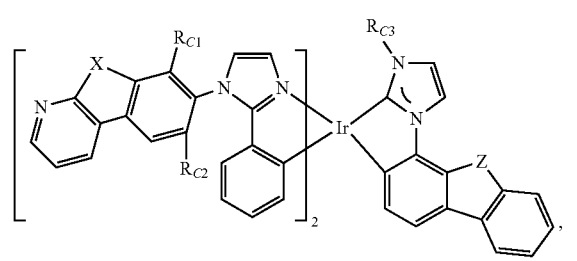

Compound 44-X

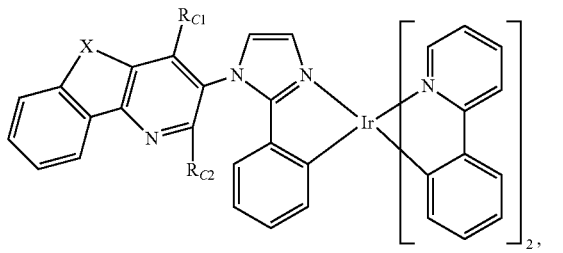

Compound 45-X

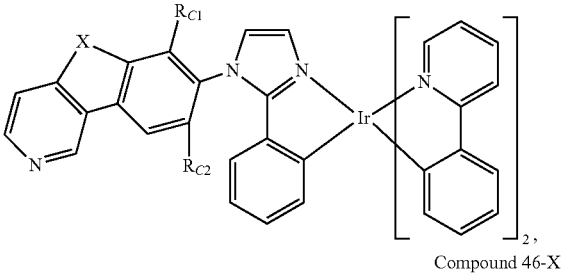

Compound 46-X

Compound 47-X

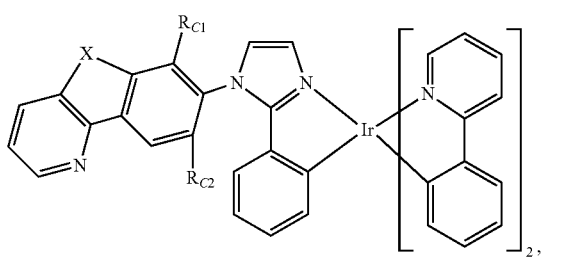

wherein $R_{C1}$, $R_{C2}$, $R_{C3}$ and $R_{C4}$ are each independently selected from the group consisting of alkyl, cycloalkyl, aryl, heteroaryl, and combinations thereof; and X and Z are O or S.

9. The compound of claim 8, wherein $R_{C1}$, $R_{C2}$, $R_{C3}$ and $R_{C4}$ are each independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof; and wherein any group is optionally partially or fully deuterated.

10. The compound of claim 1, which is selected from the group consisting of:

Compound 1-O-1

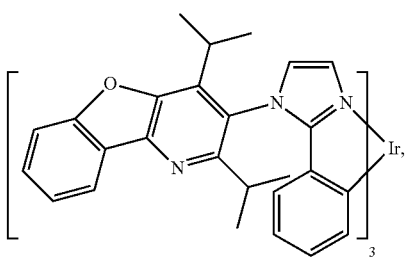

-continued

Compound 2-O-1
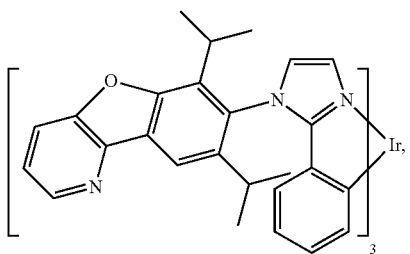

Compound 3-O-1
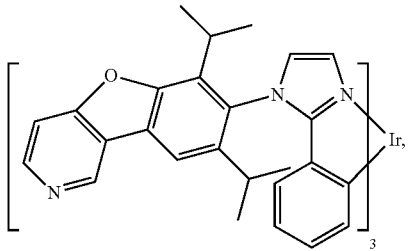

Compound 4-O-1
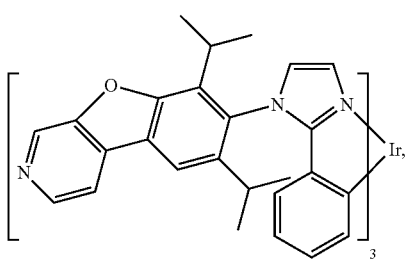

Compound 5-O-1
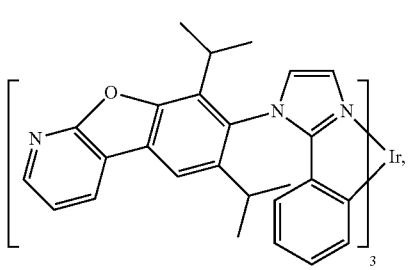

Compound 1-S-1
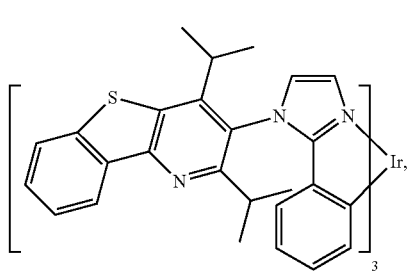

Compound 2-S-1
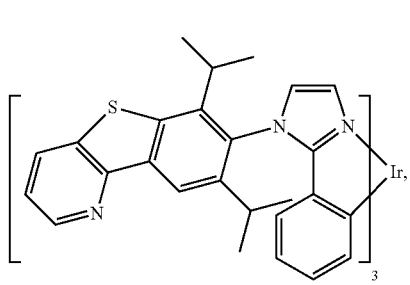

-continued

Compound 3-S-1
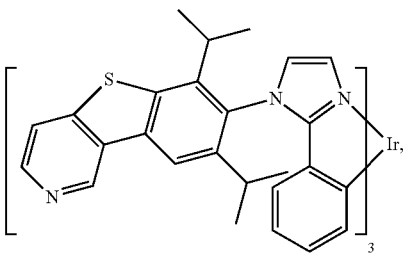

Compound 4-S-1
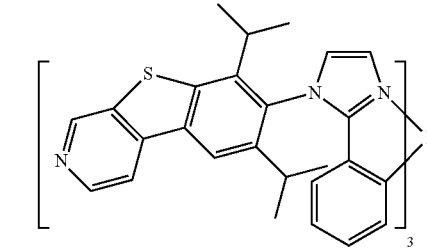

and

Compound 5-S-1

11. The compound of claim 1, wherein Z is selected from the group consisting of BR, PR, O, S, Se, C=O, S=O, SO$_2$, SiRR', and GeRR'.

12. The compound of claim 1, wherein one of $Z^1$, $Z^2$, $Z^3$, and $Z^4$ is N.

13. The compound of claim 1, wherein $Z^9Z^{10}$ is selected from the group consisting of 1-phenylimidazole, 2-phenylpyridyl, 1-(4-dibenzofuran)imidazole, and 1-(4-dibenzothiophene)imidazole, each of which is optionally substituted one or more times by substituents selected independently from the group consisting of alkyl, cycloalkyl, aryl, heteroaryl, and combinations thereof.

14. A first device comprising a first organic light emitting device, which further comprises:
   an anode;
   a cathode; and
   an organic layer disposed between the anode and the cathode, which comprises a compound having a structure of Formula (III):

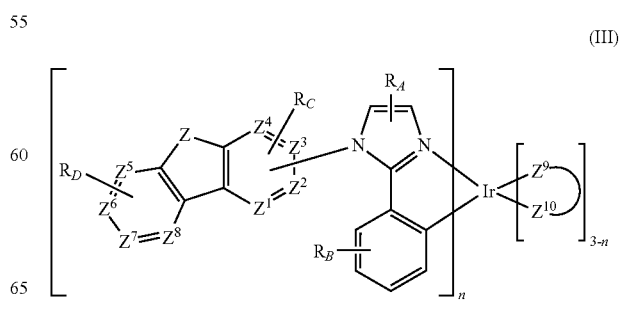

(III)

wherein $Z^9$-$Z^{19}$ is a bidentate ligand;
wherein n is 1, 2, or 3;
wherein $R_B$ and $R_D$ each represent mono, di, tri, tetra substitutions, or no substitution;
wherein $R_A$ represents mono, di, or no substitution;
wherein $R_C$ represents mono, di, tri, or no substitution;
wherein $Z^1$, $Z^2$, $Z^3$, $Z^4$, $Z^5$, $Z^6$, $Z^7$, and $Z^8$ are each selected from N or C;
wherein at least one of $Z^1$, $Z^2$, $Z^3$, $Z^4$, $Z^5$, $Z^6$, $Z^7$, and $Z^8$ is N;
wherein one of $Z^1$, $Z^2$, $Z^3$, and $Z^4$ is C that is bonded to N of A;
wherein Z is selected from the group consisting of BR, PR, O, S, Se, C=O, S=O, $SO_2$, CRR', SiRR', and GeRR';
wherein R, R', $R_A$, $R_B$, $R_C$, and $R_D$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein any two adjacent R, $R_A$, $R_C$, and $R_D$ are optionally joined to form a ring, which may be further substituted;
wherein the ligands may be linked with other ligands to form a tetradentate or hexadentate ligand;
wherein:
  if $Z^1$ is bonded to N of ring A, then $Z^2$ is CR";
  if $Z^2$ is bonded to N of ring A, then both $Z^1$ and $Z^3$ are CR";
  if $Z^3$ is bonded to N of ring A, then both $Z^2$ and $Z^4$ are CR"; or
  if $Z^4$ is bonded to N of ring A, then $Z^3$ is CR"; and
wherein R" is alkyl, cycloalkyl, aryl, or substituted aryl.

15. The first device of claim 14, wherein the first device is a consumer product selected from the group consisting of flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, wall, theater or stadium screens, and signs.

16. The first device of claim 14, wherein the organic layer is an emissive layer and the compound is an emissive dopant.

17. The first device of claim 14, wherein the organic layer is an emissive layer and the compound is a non-emissive dopant.

18. The first device of claim 14, wherein the organic layer further comprises a host.

19. The first device of claim 18, wherein the host comprises a triphenylene containing benzo-fused thiophene or benzo-fused furan;
  wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡$CC_nH_{n2+1}$, $Ar_1$, $Ar_1$-$Ar_2$, and $C_nH_{2n}$—$Ar_1$;
  wherein n is from 1 to 10; and
  wherein $Ar_1$ and $Ar_2$ are independently selected from the group consisting of benzene, biphenyl, naphthalene, triphenylene, carbazole, and heteroaromatic analogs thereof.

20. The first device of claim 18, wherein the host comprises a compound selected from the group consisting of:

carbazole, dibenzothiophene, dibenzofuran, dibenzoselenophene, azacarbazole, aza-dibenzothiophene, aza-dibenzofuran, and aza-dibenzoselenophene.

21. The first device of claim 18, wherein the host is selected from the group consisting of:

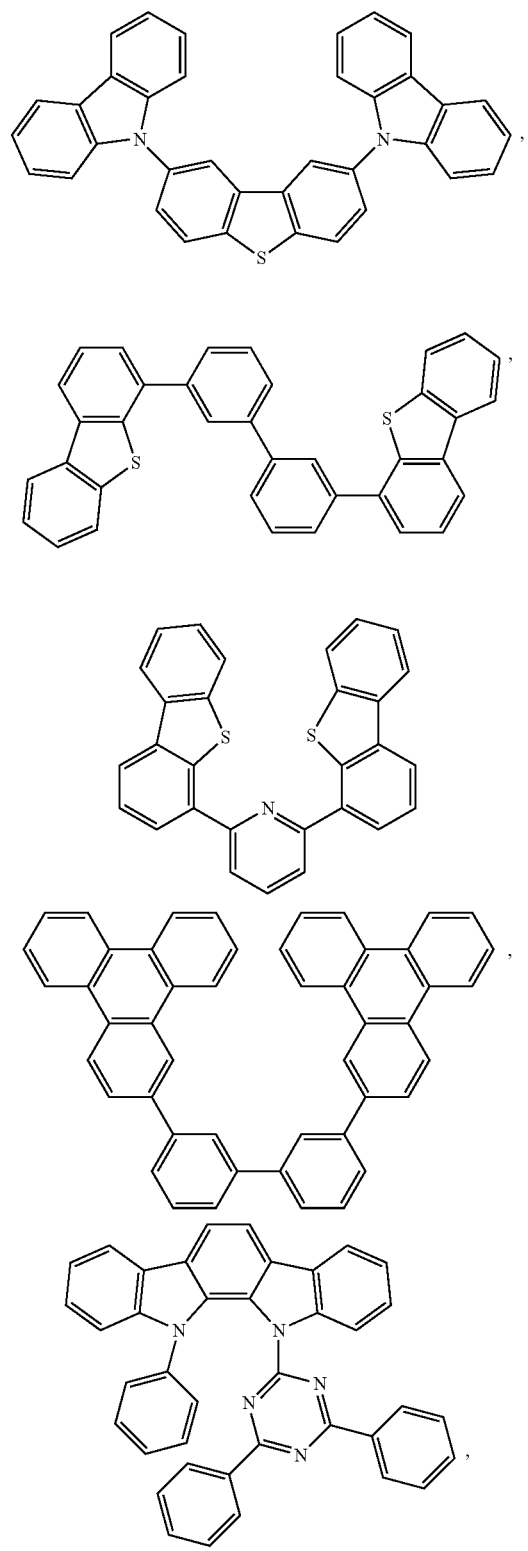

-continued
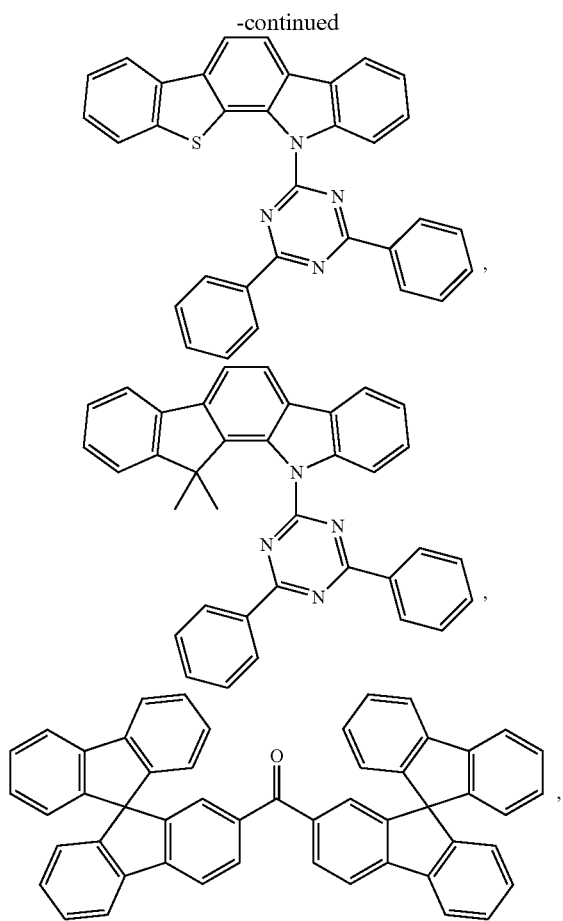
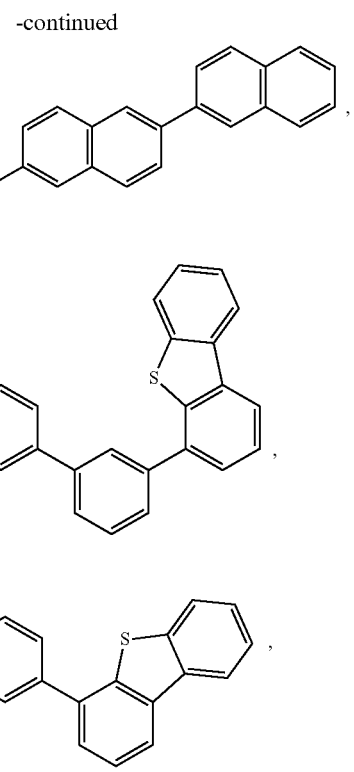
and combinations thereof.
22. The first device of claim 18, wherein the host comprises a metal complex.
* * * * *

UNITED STATES PATENT AND TRADEMARK OFFICE
CERTIFICATE OF CORRECTION

PATENT NO. : 9,978,958 B2
APPLICATION NO. : 13/798668
DATED : May 22, 2018
INVENTOR(S) : Chuanjun Xia et al.

Page 1 of 2

It is certified that error appears in the above-identified patent and that said Letters Patent is hereby corrected as shown below:

In the Claims

In Claim 1, Column 127, Lines 56-66, please delete the compound:

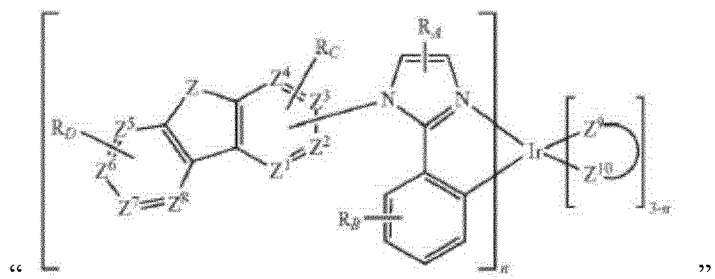

"

And insert:

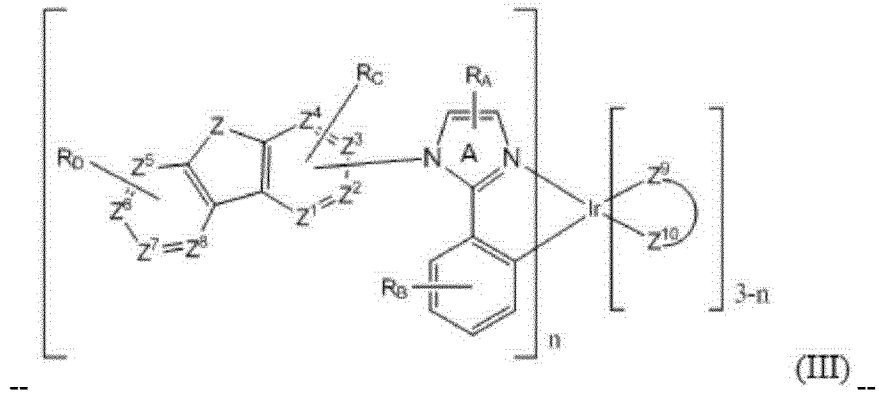

--

Signed and Sealed this
Twenty-fourth Day of July, 2018

Andrei Iancu
*Director of the United States Patent and Trademark Office*

CERTIFICATE OF CORRECTION (continued)
U.S. Pat. No. 9,978,958 B2

In Claim 14, Column 140, Lines 56-66, please delete the compound:

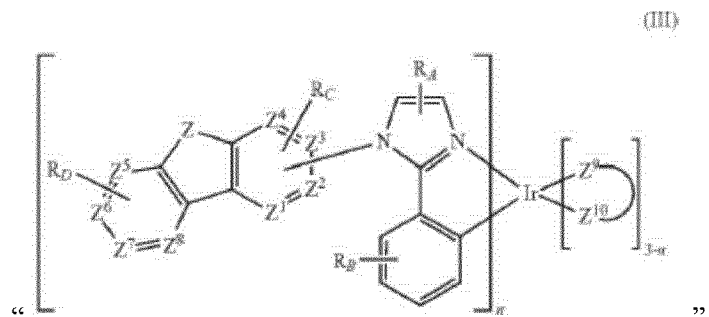

"

"

And insert:

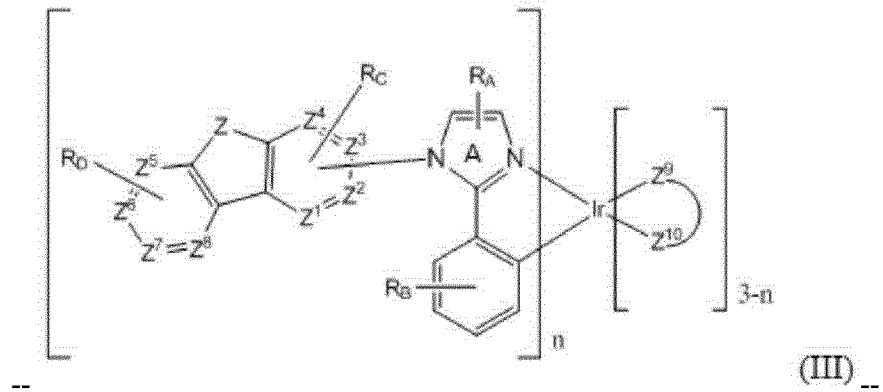

--                                                                                      (III) --